US010213160B2

(12) United States Patent
Hacker et al.

(10) Patent No.: US 10,213,160 B2
(45) Date of Patent: Feb. 26, 2019

(54) ENDOTRACHEAL TUBE APPARATUS

(71) Applicant: MEDTRONIC XOMED, INC., Jacksonville, FL (US)

(72) Inventors: David C. Hacker, Jacksonville, FL (US); Maria Charles Vijay Stanislaus, Irvine, CA (US); Wenjeng Li, Saint Johns, FL (US); Dwayne S. Yamasaki, St. Augustine, FL (US); William C. Brunnett, Mission Viejo, CA (US); Kevin L. McFarlin, St. Johns, FL (US); James Britton Hissong, Jacksonville, FL (US); Robert K. Vaccaro, Ponte Vedra Beach, FL (US); John M. Murphy, Jacksonville, FL (US); Carla A. Pagotto, Ponte Vedra Beach, FL (US); Tino Schuler, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 15/682,767

(22) Filed: Aug. 22, 2017

(65) Prior Publication Data

US 2017/0347958 A1 Dec. 7, 2017

Related U.S. Application Data

(63) Continuation of application No. 14/716,351, filed on May 19, 2015, now Pat. No. 9,918,675, which is a
(Continued)

(51) Int. Cl.
*A61B 5/00* (2006.01)
*A61B 1/00* (2006.01)
(Continued)

(52) U.S. Cl.
CPC ........ *A61B 5/6853* (2013.01); *A61B 1/00082* (2013.01); *A61B 1/04* (2013.01);
(Continued)

(58) Field of Classification Search
CPC . A61B 1/00082; A61B 5/0488; A61B 5/0421; A61B 5/04886; A61B 5/064; A61B 5/6853; A61B 17/24
See application file for complete search history.

(56) References Cited

U.S. PATENT DOCUMENTS

| | | |
|---|---|---|
| 1,864,688 A | 6/1932 | Frank |
| 2,107,835 A | 2/1938 | Pierce |

(Continued)

FOREIGN PATENT DOCUMENTS

| | | |
|---|---|---|
| CN | 2056003 | 4/1990 |
| CN | 2232257 | 8/1996 |

(Continued)

OTHER PUBLICATIONS

Notice of Allowance for U.S. Appl. No. 14/175,165 dated May 22, 2017 (12 pages).
(Continued)

*Primary Examiner* — Max Hindenburg
(74) *Attorney, Agent, or Firm* — Dicke, Billig & Czaja, PLLC

(57) ABSTRACT

An apparatus for monitoring EMG signals of a patient's laryngeal muscles includes an endotracheal tube having an exterior surface. Conductive electrodes are formed on the endotracheal tube. The conductive electrodes are configured to receive the EMG signals from the laryngeal muscles when the endotracheal tube is placed in a trachea of the patient. At least wireless sensor is formed on the endotracheal tube, and is configured to wirelessly transmit information to a processing apparatus.

20 Claims, 22 Drawing Sheets

Related U.S. Application Data continuation of application No. 12/896,578, filed on Oct. 1, 2010, now Pat. No. 9,037,226.

(60) Provisional application No. 61/248,294, filed on Oct. 2, 2009.

(51) Int. Cl.

| | | |
|---|---|---|
| *A61B 1/267* | (2006.01) | |
| *A61B 5/0488* | (2006.01) | |
| *A61B 5/06* | (2006.01) | |
| *A61M 16/04* | (2006.01) | |
| *A61N 1/05* | (2006.01) | |
| *A61B 5/0492* | (2006.01) | |
| *A61B 1/04* | (2006.01) | |
| *A61B 1/07* | (2006.01) | |
| *A61B 5/01* | (2006.01) | |
| *A61B 5/04* | (2006.01) | |
| *A61B 5/07* | (2006.01) | |
| *A61B 5/11* | (2006.01) | |
| *A61B 5/042* | (2006.01) | |
| *A61B 1/005* | (2006.01) | |
| *A61B 1/015* | (2006.01) | |
| *A61B 1/018* | (2006.01) | |
| *A61M 16/08* | (2006.01) | |

(52) U.S. Cl.
CPC .............. *A61B 1/07* (2013.01); *A61B 1/267* (2013.01); *A61B 1/2673* (2013.01); *A61B 5/01* (2013.01); *A61B 5/04012* (2013.01); *A61B 5/0488* (2013.01); *A61B 5/0492* (2013.01); *A61B 5/04886* (2013.01); *A61B 5/062* (2013.01); *A61B 5/064* (2013.01); *A61B 5/065* (2013.01); *A61B 5/07* (2013.01); *A61B 5/11* (2013.01); *A61M 16/04* (2013.01); *A61M 16/0434* (2013.01); *A61M 16/0443* (2014.02); *A61M 16/0445* (2014.02); *A61M 16/0459* (2014.02); *A61M 16/0463* (2013.01); *A61M 16/0488* (2013.01); *A61N 1/0517* (2013.01); *A61N 1/0519* (2013.01); *A61B 1/005* (2013.01); *A61B 1/00147* (2013.01); *A61B 1/015* (2013.01); *A61B 1/018* (2013.01); *A61B 5/0421* (2013.01); *A61B 2562/0209* (2013.01); *A61B 2562/0215* (2017.08); *A61B 2562/0219* (2013.01); *A61B 2562/0261* (2013.01); *A61B 2562/046* (2013.01); *A61M 16/0411* (2014.02); *A61M 16/0825* (2014.02); *A61M 2205/0233* (2013.01); *A61M 2205/0294* (2013.01); *A61M 2205/332* (2013.01); *A61M 2205/3306* (2013.01); *A61M 2205/3344* (2013.01); *A61M 2205/3368* (2013.01); *A61M 2205/3546* (2013.01); *A61M 2205/3569* (2013.01); *A61M 2205/3592* (2013.01); *A61M 2205/6054* (2013.01); *A61M 2210/065* (2013.01); *A61M 2230/08* (2013.01)

(56) References Cited

U.S. PATENT DOCUMENTS

| | | |
|---|---|---|
| 2,429,585 A | 10/1947 | Rogoff |
| 2,618,684 A | 11/1952 | Bergan |
| 2,872,505 A | 2/1959 | Ustin |
| 3,165,575 A | 1/1965 | Lynch, Jr. et al. |
| 3,494,364 A | 2/1970 | Peters |
| 3,734,094 A | 5/1973 | Calinog |
| 3,783,178 A | 1/1974 | Philibert et al. |
| 3,892,455 A | 7/1975 | Sotolongo |
| 3,951,136 A | 4/1976 | Wall |
| 4,090,518 A | 5/1978 | Elam |
| 4,176,660 A | 12/1979 | Mylrea et al. |
| 4,231,365 A | 11/1980 | Scarberry |
| 4,304,239 A | 12/1981 | Perlin |
| 4,349,031 A | 9/1982 | Perlin |
| 4,369,794 A | 1/1983 | Furler |
| 4,461,304 A | 7/1984 | Kuperstein |
| 4,647,713 A | 3/1987 | de Nijis et al. |
| 4,776,808 A | 10/1988 | Davidson |
| 4,836,214 A | 6/1989 | Sramek |
| 4,863,390 A | 9/1989 | Cera et al. |
| 4,890,623 A | 1/1990 | Cook et al. |
| 4,906,244 A | 3/1990 | Pinchuk et al. |
| 4,960,133 A | 10/1990 | Hewson |
| 4,967,759 A | 11/1990 | Teves |
| 5,024,228 A | 6/1991 | Goldstone et al. |
| 5,096,445 A | 3/1992 | Lostumo |
| 5,125,406 A | 6/1992 | Goldstone et al. |
| 5,135,001 A | 8/1992 | Sinofsky et al. |
| 5,170,803 A | 12/1992 | Hewson et al. |
| 5,286,211 A | 2/1994 | McIntosh |
| 5,364,281 A | 11/1994 | Leto |
| 5,379,765 A | 1/1995 | Kajiwara et al. |
| 5,429,617 A | 7/1995 | Hammersmark |
| 5,464,404 A | 11/1995 | Abela et al. |
| 5,554,176 A | 9/1996 | Maddison et al. |
| 5,584,290 A | 12/1996 | Brain |
| 5,672,065 A | 9/1997 | Womack |
| 5,782,744 A | 7/1998 | Money |
| 5,782,774 A | 7/1998 | Shmulewitz |
| 5,785,051 A | 7/1998 | Lipscher et al. |
| 5,836,874 A | 11/1998 | Swanson et al. |
| 5,864,093 A | 1/1999 | Hecock et al. |
| 5,924,984 A | 7/1999 | Rao |
| 5,972,026 A | 10/1999 | Laufer et al. |
| 6,010,500 A | 1/2000 | Sherman et al. |
| 6,032,065 A | 2/2000 | Brown |
| 6,062,223 A | 5/2000 | Palazzo et al. |
| 6,095,987 A | 8/2000 | Shmulewitz et al. |
| 6,142,993 A | 11/2000 | Whayne et al. |
| 6,148,222 A | 11/2000 | Ramsey, III |
| 6,226,548 B1 | 5/2001 | Foley et al. |
| 6,259,938 B1 | 7/2001 | Zarychta et al. |
| 6,266,548 B1 | 7/2001 | Lamade et al. |
| 6,266,549 B1 | 7/2001 | Melnikoff et al. |
| 6,292,701 B1 | 9/2001 | Prass et al. |
| 6,334,068 B1 | 12/2001 | Hacker |
| 6,343,233 B1 | 1/2002 | Werner et al. |
| 6,357,447 B1 | 3/2002 | Swanson et al. |
| 6,443,156 B1 | 9/2002 | Niklason et al. |
| 6,463,327 B1 * | 10/2002 | Lurie .................... A61H 31/00 607/42 |
| 6,547,788 B1 | 4/2003 | Maguire et al. |
| 6,584,347 B1 | 6/2003 | Sinderby |
| 6,626,841 B1 | 9/2003 | Atlee, III |
| 6,626,899 B2 | 9/2003 | Houser et al. |
| 6,735,471 B2 | 5/2004 | Hill et al. |
| 6,869,431 B2 | 3/2005 | Maguire et al. |
| 6,877,512 B2 | 4/2005 | Imai et al. |
| 6,976,857 B1 | 12/2005 | Shukla |
| 7,008,419 B2 | 3/2006 | Shadduck |
| 7,146,222 B2 | 12/2006 | Boling |
| 7,153,146 B2 | 12/2006 | Shimizu et al. |
| 7,179,345 B2 | 2/2007 | Shkolnik |
| 7,216,001 B2 | 5/2007 | Hacker et al. |
| 7,293,562 B2 | 11/2007 | Malecki et al. |
| 7,507,239 B2 | 3/2009 | Shadduck |
| 7,583,991 B2 | 9/2009 | Rea |
| 7,736,362 B2 | 6/2010 | Eberl et al. |
| 7,794,256 B1 | 9/2010 | Sochor |
| 7,972,308 B2 | 7/2011 | Putz |
| 8,145,289 B2 | 3/2012 | Calabro' et al. |
| 8,152,803 B2 | 4/2012 | Edwards et al. |
| 8,224,422 B2 | 7/2012 | Mottola et al. |
| 8,352,012 B2 | 1/2013 | Besio |
| 8,467,844 B2 | 6/2013 | Rea et al. |
| 8,634,894 B2 | 1/2014 | Rea et al. |
| 8,688,237 B2 | 4/2014 | Stanislaus et al. |

(56) References Cited

U.S. PATENT DOCUMENTS

| | | |
|---|---|---|
| 8,886,280 B2 | 11/2014 | Kartush |
| 9,037,226 B2 | 5/2015 | Hacker et al. |
| 9,060,744 B2 | 6/2015 | Li |
| 9,289,141 B2 | 3/2016 | Lowery et al. |
| 9,398,865 B2 | 7/2016 | Li |
| 9,763,624 B2 | 9/2017 | Stanislaus et al. |
| 9,907,484 B2 | 3/2018 | Li |
| 9,913,594 B2 | 3/2018 | Li et al. |
| 9,918,675 B2 | 3/2018 | Hacker et al. |
| 9,918,676 B2 | 3/2018 | Hacker |
| 9,931,079 B2 | 4/2018 | Li et al. |
| 2001/0018281 A1 | 8/2001 | Royer |
| 2002/0016615 A1 | 2/2002 | Dev et al. |
| 2002/0032468 A1 | 3/2002 | Hill et al. |
| 2002/0188332 A1 | 12/2002 | Lurie et al. |
| 2003/0018327 A1 | 1/2003 | Truckai et al. |
| 2003/0074039 A1 | 4/2003 | Puskas |
| 2004/0186461 A1 | 9/2004 | DiMatteo |
| 2004/0230110 A1 | 11/2004 | Sinderby et al. |
| 2005/0085111 A1 | 4/2005 | Clark et al. |
| 2005/0113686 A1 | 5/2005 | Peckham |
| 2005/0159659 A1 | 7/2005 | Sawan et al. |
| 2005/0222656 A1 | 10/2005 | Wahlstrand et al. |
| 2005/0255727 A1 | 11/2005 | Alladice |
| 2006/0012671 A1 | 1/2006 | Nimri et al. |
| 2006/0025702 A1 | 2/2006 | Sterrantino et al. |
| 2006/0116564 A1 | 6/2006 | Mintchev et al. |
| 2006/0241725 A1 | 10/2006 | Libbus et al. |
| 2006/0254595 A1 | 11/2006 | Rea |
| 2007/0074728 A1 | 4/2007 | Rea |
| 2007/0137651 A1 | 6/2007 | Glassenberg et al. |
| 2007/0142888 A1 | 6/2007 | Chavez |
| 2007/0156041 A1 | 7/2007 | Rea |
| 2007/0170928 A1 | 7/2007 | Fedan et al. |
| 2007/0219551 A1 | 9/2007 | Honour et al. |
| 2008/0077043 A1 | 3/2008 | Malbrain et al. |
| 2008/0140052 A1 | 6/2008 | Moller et al. |
| 2008/0177190 A1 | 7/2008 | Libbus et al. |
| 2008/0249507 A1 | 10/2008 | Hadani |
| 2008/0255441 A1 | 10/2008 | Hadani |
| 2008/0300650 A1 | 12/2008 | Gerber et al. |
| 2009/0227885 A1 | 9/2009 | Lowery et al. |
| 2010/0006103 A1 | 1/2010 | McGinnis et al. |
| 2010/0036229 A1 | 2/2010 | Weekamp et al. |
| 2010/0063376 A1 | 3/2010 | Kartush |
| 2010/0087782 A1 | 4/2010 | Ghaffari et al. |
| 2010/0145178 A1 | 6/2010 | Kartush |
| 2010/0168561 A1 | 7/2010 | Anderson |
| 2010/0168743 A1 | 7/2010 | Stone et al. |
| 2010/0179417 A1 | 7/2010 | Russo |
| 2010/0191311 A1 | 7/2010 | Scheiner |
| 2010/0198099 A1 | 8/2010 | Murphy et al. |
| 2010/0317956 A1 | 12/2010 | Kartush |
| 2011/0023889 A1 | 2/2011 | Lin et al. |
| 2011/0030694 A1 | 2/2011 | Schaner et al. |
| 2011/0071379 A1 | 3/2011 | Rea et al. |
| 2011/0190596 A1 | 8/2011 | Hacker et al. |
| 2011/0230734 A1 | 9/2011 | Fain et al. |
| 2011/0245647 A1 | 10/2011 | Stanislaus et al. |
| 2011/0301587 A1 | 12/2011 | Deem et al. |
| 2011/0306861 A1 | 12/2011 | Thramann et al. |
| 2012/0016256 A1 | 1/2012 | Mabary et al. |
| 2012/0024292 A1 | 2/2012 | Sandmore et al. |
| 2012/0055257 A1 | 3/2012 | Shaw-Klein |
| 2013/0172714 A1 | 7/2013 | Li et al. |
| 2014/0148672 A1 | 5/2014 | Li |
| 2014/0155720 A1 | 6/2014 | Stanislaus et al. |
| 2014/0275914 A1 | 9/2014 | Li et al. |
| 2015/0250423 A1 | 9/2015 | Hacker et al. |
| 2016/0038072 A1 | 2/2016 | Brown et al. |
| 2016/0038073 A1 | 2/2016 | Brown et al. |
| 2016/0038074 A1 | 2/2016 | Brown et al. |
| 2016/0262699 A1 | 9/2016 | Goldstone et al. |
| 2016/0287112 A1 | 10/2016 | McFarlin et al. |
| 2016/0287861 A1 | 10/2016 | McFarlin et al. |
| 2016/0324475 A1 | 11/2016 | Hacker |
| 2016/0345905 A1 | 12/2016 | Li |
| 2017/0007146 A1 | 1/2017 | Schulhauser et al. |

FOREIGN PATENT DOCUMENTS

| | | |
|---|---|---|
| CN | 2827273 | 10/2006 |
| DE | 29751344 | 1/1988 |
| DE | 19750705 | 3/2000 |
| EP | 0438863 | 11/1990 |
| EP | 1750368 A1 | 2/2007 |
| GB | 1214718 | 12/1970 |
| JP | H03-182230 | 8/1991 |
| JP | 2001-224554 | 8/2001 |
| JP | 2003-019200 | 1/2003 |
| JP | 2003-527164 | 9/2003 |
| JP | 2006-528890 | 12/2006 |
| JP | 2007-307185 | 11/2007 |
| JP | 2007-532152 | 11/2007 |
| JP | 2009-519763 | 5/2009 |
| JP | 2009-524482 | 7/2009 |
| KR | 1020060031799 | 4/2006 |
| WO | 199723163 | 7/1997 |
| WO | 200141638 | 6/2001 |
| WO | 2004/100786 | 11/2004 |
| WO | 2005/097246 | 10/2005 |
| WO | 2006012671 | 2/2006 |
| WO | 2006012672 | 2/2006 |
| WO | 2007/078827 | 7/2007 |
| WO | 2007/089491 | 8/2007 |
| WO | 2008/091928 | 7/2008 |
| WO | 2011/041690 | 4/2011 |
| WO | 2013/008106 | 1/2013 |

OTHER PUBLICATIONS

U.S. Appl. No. 15/217,572, filed Jul. 22, 2016, Inventor: David C. Hacker (65 pages).
Non-Final Office Action for U.S. Appl. No. 15/217,572 dated Feb. 9, 2017 (13 pages).
Final Office Action for U.S. Appl. No. 15/217,572 dated Jun. 6, 2017 (22 pages).
Non-Final Office Action for U.S. Appl. No. 13/343,283, dated Oct. 2, 2014 (26 pages).
Final Office Action for U.S. Appl. No. 13/343,283, dated May 26, 2015 (18 pages).
Advisory Action for U.S. Appl. No. 13/343,283, dated Aug. 28, 2015 (4 pages).
Non-Final Office Action for U.S. Appl. No. 13/343,283, dated Jan. 13, 2016 (19 pages).
Final Office Action for U.S. Appl. No. 13/343,283 dated Jul. 15, 2016 (22 pages).
Advisory Action for U.S. Appl. No. 13/343,283 dated Sep. 26, 2016 (4 pages).
Office Action for U.S. Appl. No. 13/343,283 dated Jan. 6, 2017 (24 pages).
Electric Motion Company, webpage "Telephony & CATV Products [Bronze Vise Type Connectors]" published Aug. 19, 2007, retrieved via Wayback Machine Jun. 20, 2016 (11 pages).
Southern Grounding Products, webpage "Grounding & ground Rod Clamps" published Nov. 19, 2008, retrieved via Wayback Machine Jun. 20, 2016 (5 pages).
Australian 1st Examination Report for 2012363699 dated Sep. 8, 2016 (3 pages). (.141).
Chinese 1st Office Action for 201280071074.3 dated Oct. 30, 2015 (12 pages). (.231).
Japanese 1st Office Action for 2014-551252 dated Oct. 20, 2016 (3 pages). (.441).
Australian 2nd Examination Report for 2012363699 dated Jun. 22, 2017 (6 pages). (.141).
Non-Final Office Action for U.S. Appl. No. 13/688,818 dated Mar. 13, 2014 (10 pages).
Final Office Action for U.S. Appl. No. 13/688,818 dated Jun. 25, 2014 (10 pages).

(56) References Cited

OTHER PUBLICATIONS

Non-Final Office Action for U.S. Appl. No. 13/688,818 dated Oct. 9, 2014 (7 pages).
Notice of Allowance for U.S. Appl. No. 13/688,818 dated Feb. 20, 2015 (7 pages).
International Search Report and Written Opinion, PCT/US2013/072193, dated Mar. 11, 2014 (18 pages).
Australian 1st Examination Report for 2013406220 dated May 19, 2016 (3 pages). (.141).
Non-Final Office Action for U.S. Appl. No. 14/747,257 dated Nov. 17, 2015 (10 pages).
Notice of Allowance for U.S. Appl. No. 14/747,257 dated Mar. 23, 2016 (5 pages).
Final Office Action for U.S. Appl. No. 15/219,726 dated Oct. 21, 2016 (34 pages).
Advisory Action for U.S. Appl. No. 15/219,726 dated Jan. 5, 2017 (4 pages).
Non-Final Office Action for U.S. Appl. No. 15/219,726 dated Apr. 11, 2017 (23 pages).
European Office Action for Application No. 14720826.8, dated Aug. 2, 2016 (8 pgs).
European Office Action for Application No. 14720826.8, dated Feb. 1, 2017 (6 pgs).
Defendants' Invalidity Contentions and Document Production Pursuant to Patent Local Rules 3-3 and 3-4; *Neurovision Medical Products, Inc.* v. *Medtronic Public Limited Company, Medtronic, Inc.; Medtronic Xomed, Inc. HCA Holdings, Inc.; and Healthtrust Purchasing Group, L.P.*; Civ. No. 2:16-cv-00127-JRP-RSP, signed by James M. Hilmert, date Jun. 10, 2016 (147 pages).
Hon, Li & Hutchings, "Direct writing technology—Advances and developments," CIRP Annals—Manufacturing Technology, vol. 57, Issue 2, presented on Aug. 25, 2008 and published Oct. 28, 2008, pp. 601-620 (20 pages).
Kartush et al., "Intraoperative Facial Nerve Monitoring," Ch. 5, Neuromonitoring in Otology and Head and Neck Surgery, Raven Press, Ltd., p. 99-120 (1992) (22 pages).
Goldstone A., Schettino R., "The Electrode Endotracheal Tube: A State of the Art Method for Monitoring the Recurrent Laryngeal Nerve-Vocal Cord Muscle Integrity in the Intubated Patient," presented to the American Academy of Otolaryngology/Head & Neck Surgery Annual National Meeting, San Diego, CA. (Sep. 1990) (1 page).
Eisele D.W., Goldstone A., "Electrophysiologic Identification and Preservation of the Superior Laryngeal Nerve During Thyroid Surgery," The Laryngescope, vol. 101, Issue 3, pp. 313-315 (Mar. 1991) (3 pages).
Bakhshaee et al., "Evaluation of the Distance Between Anterior Commissure of True Vocal Folds and the First Tracheal Ring and Related Laryngeal Indices in 40 Human Cadavers," J. Voice, vol. 30, No. 2, p. 159, col. 1 (2016) (3 pages).
Sprinzl et al., "Morphometric Measurements of the Cartilaginous Larynx: an Anatomic Correlate of Laryngeal Surgery," Head & Neck, Figs. 3-4, Tables 2-3, p. 743-750 (Dec. 1999) (8 pages).
Witt, Robert L., "Recurrent Laryngeal Nerve Electrophysiologic Monitoring in Thyroid Surgery: The Standard of Care?" J. Voice, vol. 19, No. 3, pp. 497-500 (2005) (4 pages).
Strauss, Christian et al., "Electrophysiological Localization of Motor Areas within the Rhomboid Fossa During Brainstem Surgery," ECoG, OAE and Intraoperative Monitoring: Proceedings of the First International Conference, (D. Höhmann, ed.) pp. 375-378 (Sep. 1992) (10 pages).
Møller, Aage R., "Monitoring and Mapping the Cranial Nerves and the Brainstem," Ch. 13, Neurophysiology in Neurosurgery: A Modern Intraoperative Approach, Academic Press, pp. 291-318 (2002) (36 pages).
Wang et al., "Prognostic Indicators of Unilateral Vocal Fold Paralysis," Archives of Otolaryngology Head Neck Surgery, vol. 134, No. 4, pp. 380-388 (Apr. 2008) (11 pages).
Dimopoulos et al., "Quantitative Estimation of the Recurrent Laryngeal Nerve Irritation by Employing Spontaneous Intraoperative Electromyographic Monitoring During Anterior Cervical Discectomy and Fusion," J. Spinal Disorder Tech, vol. 22, No. 1, pp. 1-7 (Feb. 2009) (7 pages).
Ajmani, M. L., "A Metrical Study of the Laryngeal Skeleton in Adult Nigerians," J. Anat, vol. 171, pp. 187-191 (1990) ("Ajmani Article") (5 pages).
Grillo, Hermes, Surgery of the Trachea and Bronchi, BC Decker Inc., pp. 39-59 (2004) (23 pages).
Livingstone, Churchill, Gray's Anatomy, pp. 1637-1657 (1995) (28 pages).
Special 510(k) Premarket Notification, K094054, Neurovision® EMG Endotracheal Tube dated May 14, 2010 (6 pages).
Pictures of a NuVasive EMG tube (5 pages). The first public use of the NuVasive EMG tube is unclear to Applicant. For purposes of Examination only, the NuVasive EMG tube may be considered to be prior art to the present application, although Applicant reserves the right to challenge this in any future proceeding. Applicant has submitted a physical sample of the NuVasive EMG tube in U.S. Appl. No. 15/217,572, filed Jul. 22, 2016.
David L. Bourell et al., Solid Freeform Fabrication Proceedings, Aug. 2004, © 2004 The University of Texas at Austin (15 pages).
ECOM™ Brochure for Endotracheal Cardiac Output Monitor, © 2008 ConMed Corporation Sep. 2008 (2 pages).
James K. Brown et al., Parasympathetic Innervation of the Cervical Trachealis Muscle in Living Dogs, © 1982 The American Physiology Society, vol. 53, No. 3, pp. 617-625 (9 pages).
Notice of Allowance for U.S. Appl. No. 14/716,351 dated Jan. 22, 2018 (12 pages).
Notice of Allowance for U.S. Appl. No. 15/217,572 dated Jan. 22, 2018 (9 pages).
Notice of Allowance for U.S. Appl. No. 13/343,283 dated Jan. 19, 2018 (12 pages).
Notice of Allowance for U.S. Appl. No. 15/219,726 dated Dec. 20, 2017 (15 pages).
Notice of Allowance for U.S. Appl. No. 13/826,323 dated Dec. 19, 2017 (10 pages).
Restriction Requirement for U.S. Appl. No. 12/896,578 dated Jul. 24, 2012 (8 pages).
Non-Final Office Action for U.S. Appl. No. 12/896,578 dated Oct. 3, 2012 (16 pages).
Non-Final Office Action for U.S. Appl. No. 12/896,578 dated Sep. 19, 2013 (16 pages).
Notice of Allowance for U.S. Appl. No. 12/896,578 dated Feb. 27, 2014 (7 pages).
Notice of Allowance for U.S. Appl. No. 12/896,578 dated Jun. 9, 2014 (11 pages).
Notice of Allowance for U.S. Appl. No. 12/896,578 dated Aug. 5, 2014 (12 pages).
Notice of Allowance for U.S. Appl. No. 12/896,578 dated Oct. 6, 2014 (11 pages).
Notice of Allowance for U.S. Appl. No. 12/896,578 dated Jan. 28, 2015 (12 pages).
Notice of Allowance for U.S. Appl. No. 12/896,578 dated Mar. 30, 2015 (11 pages).
PCT Search Report dated Apr. 28, 2011 for PCT/US2010/051132 (17 pages).
International Preliminary Report on Patentability for PCT/US2010/051132, dated Dec. 5, 2011 (5 pages).
Australian Examination Report dated Feb. 25, 2013 (4 pages) re 2010300373.
Canadian 1st Examiner's Report for 2775588 dated Oct. 28, 2016 (4 pages). (.211).
Chinese 1st Office Action for 201080054559.2 dated Feb. 14, 2014 (5 pages).
Chinese 2nd Office Action for Application No. 201080054559.2, dated Jul. 17, 2014 (10 pages).
Japanese Office Action for Application No. 2012/532,355, dated Apr. 18, 2014 (7 pages).
European Examination Report for Application No. 10781544.1, dated Feb. 19, 2014 (4 pages). (.291).
Extended European Search Report for Serial No. 14182496.1, dated Nov. 28, 2014 (7 pages). (.292).

(56) References Cited

OTHER PUBLICATIONS

Korean 1st Office Action for 10-2012-7011251 dated Feb. 6, 2017 (13 pages).
Restriction Requirement for U.S. Appl. No. 14/716,351 dated Jan. 22, 2016 (5 pages).
Non-Final Office Action for U.S. Appl. No. 14/716,351 dated May 3, 2016 (25 pages).
Non-Final Office Action for U.S. Appl No. 14/716,351 dated Sep. 21, 2016 (6 pages).
Final Office Action for U.S. Appl. No. 14/716,351 dated Mar. 21, 2017 (30 pages).
Non-Final Office Action for U.S. Appl. No. 14/716,351 dated May 17, 2017 (13 pages).
Non-Final Office Action for U.S. Appl. No. 12/896,593 dated Sep. 5, 2012 (17 pages).
Final Office Action for U.S. Appl. No. 12/896,593, dated Jan. 3, 2013 (13 pages).
Advisory Action for U.S. Appl. No. 12/896,593 dated Apr. 10, 2013 (7 pages).
Notice of Allowance for U.S. Appl. No. 12/896,593 dated Aug. 15, 2013 (11 pages).
Notice of Allowance for U.S. Appl. No. 12/896,593 dated Nov. 7, 2013 (13 pages).
PCT Search Report dated Feb. 4, 2011 for PCT/US2010/051145 (15 pages).
International Preliminary Report on Patentability dated Oct. 24, 2011 for PCT/US2010/051145 (12 pages).
Australian Examination Report No. 1 for Application No. 2010300379, dated May 30, 2014 (4 pages). (.141).
Australian Examination Report No. 1 for Application No. 2015200049, dated Mar. 10, 2016 (3 pages). (.142).
Canadian 1st Examiner's Report for 2776163 dated Oct. 28, 2016 (4 pages). (.211).
Chinese 1st Office Action for 201080054850.X dated Feb. 20, 2014 (19 pages).
Chinese 2nd Office Action for Application No. 201080054850.X, dated Jul. 23, 2014 (6 pages).
European Examination Report for Application No. 10779358.0, dated Feb. 19, 2014 (4 pages). (.291).
Extended European Search Report for Application No. 16176750.4, dated Nov. 22, 2016 (6 pages). (.292).
Japanese Office Action for Application No. 2012/532,356, dated Apr. 18, 2014 (7 pages).
Japanese Office Action for Application No. 2014/189873, dated Aug. 30, 2015 (5 pgs).
Notice of Allowance for U.S. Appl. No. 14/175,165 dated May 29, 2014 (28 pages).
Non-Final Office Action for U.S. Appl. No. 14/175,165, dated Aug. 15, 2014 (17 pages).
Final Office Action for U.S. Appl. No. 14/175,165, dated Dec. 4, 2014 (13 pages).
Non-Final Office Action for U.S. Appl. No. 14/175,165, dated Mar. 3, 2015 (12 pages).
Final Office Action for U.S. Appl. No. 14/175,165, dated Jun. 12, 2015 (16 pages).
Advisory Action for U.S. Appl. No. 14/175,165, dated Sep. 25, 2015 (6 pages).
Non-Final Office Action for U.S. Appl. No. 14/175,165 dated Jan. 5, 2016 (22 pages).
Final Office Action for U.S. Appl. No. 14/175,165 dated May 19, 2016 (24 pages).
Notice of Allowance for U.S. Appl. No. 14/175,165 dated Feb. 23, 2017 (13 pages).
Corrected Notice of Allowability for U.S. Appl. No. 14/175,165 dated Mar. 23, 2017 (18 pages).
NuVasive® NeuroVision® EMG Endotracheal Tube brochure—© 2010 NuVasive, Inc. (4 pages).
Cahide Topsakal et al., Intraoperative Monitoring of Lower Cranial Nerves in Skull Base Surgery: Technical Report and Review of 123 Monitored Cases, Neurosurg. Rev., vol. 31, pp. 45-52 Published Online Oct. 24, 2007 © Springer-Verlag 2007 (9 pages).
Jasper R. Daube et al., Clinical Neurophysiology, Third Edition, Oxford University Press. Chapters 25, 43 and 44, © 2009 (71 pages).
U.S. Appl. No. 61/244,402, filed Sep. 21, 2009 (11 pages).
U.S. Appl. No. 14/945,167, filed Nov. 18, 2015 (89 pages).
U.S. Appl. No. 14/945,208, filed Nov. 18, 2015 (88 pages).
Affidavit of Christopher Butler with Exhibit A dated Nov. 10, 2016 (8 pages).
Decision-Institution of Inter Partes Review; *Medtronic Xomed, Inc. v. Neurovision Medical Products, Inc.*; PTAB Case IPR2016-01405; for U.S. Pat. No. 8,634,894 entered Dec. 29, 2016 (35 pages).
Petition for Inter Partes Review; *Medtronic Xomed, Inc. v. Neurovision Medical Products, Inc.*; PTAB Case IPR2017-00456; for U.S. Pat. No. 8,634,894 dated Dec. 9, 2016 (58 pages).
Patentee's Preliminary Response to Petition for Inter Partes Review; *Medtronic Xomed, Inc. v. Neurovision Medical Products, Inc.*; PTAB Case IPR2016-01405; for U.S. Pat. No. 8,634,894 dated Oct. 20, 2016 (74 pages).
Declaration of Mike Lieu—Exhibit 2002 to Patentee's Preliminary Response to Petition for Inter Partes Review dated Oct. 20, 2016 (7 pages).
Declaration of Stephen W. Blakely—Exhibit 2003 to Patentee's Preliminary Response to Petition for Inter Partes Review dated Oct. 20, 2016 (7 pages).
Declaration of James Lee Rea—Exhibit 2004 to Patentee's Preliminary Response to Petition for Inter Partes Review dated Oct. 20, 2016 (6 pages).
Declaration of Ryan M. Rea—Exhibit 2005 to Patentee's Preliminary Response to Petition for Inter Partes Review dated Oct. 20, 2016 (2 pages).
"Thyroid Surgery May Result in Paralysis of Vocal Cords," Wall Street Journal article dated Aug. 10, 2001 to Exhibit 2006 to Patentee's Preliminary Response to Petition for Inter Partes Review dated Oct. 20, 2016 (4 pages).
Medtronic webpage at http://medtronic.com/us-en/healthcare-nim-nerve-monitoring-systems/related-nerve-monitoring-products.html—Exhibit 2007 to Patentee's Preliminary Response to Petition for Inter Partes Review dated Oct. 20, 2016 (5 pages).
Medtronic product recall notice—Exhibit 2008 to Patentee's Preliminary Response to Petition for Inter Partes Review dated Oct. 20, 2016 (4 pages).
MicroPenning: How It Works—Exhibit 2009 to Patentee's Preliminary Response to Petition for Inter Partes Review dated Oct. 20, 2016 (2 pages).
MicroPenning: Overview—Exhibit 2010 to Patentee's Preliminary Response to Petition for Inter Partes Review dated Oct. 20, 2016 (3 pages).
U.S. Pat. No. 4,461,304 to Kuperstein—Exhibit 2011 to Patentee's Preliminary Response to Petition for Inter Partes Review dated Oct. 20, 2016 (10 pages).
U.S. Appl. No. 61/126,567—Exhibit 2012 to Patentee's Preliminary Response to Petition for Inter Partes Review dated Oct. 20, 2016 (8 pages).
NuVasive, Inc.'s Petition for Inter Partes Review file in IPR2015-00502—Exhibit 2014 to Patentee's Preliminary Response to Petition for Inter Partes Review dated Oct. 20, 2016 (63 pages).
PTAB's Decision dated Jul. 16, 2015 in IPR2015-00502—Exhibit 2015 to Patentee's Preliminary Response to Petition for Inter Partes Review dated Oct. 20, 2016 (31 pages).
Table of page cites and summary regarding Exhibit 2001—Exhibit 2016 to Patentee's Preliminary Response to Petition for Inter Partes Review dated Oct. 20, 2016 (14 pages).
Redacted Exhibit 2001—Confidential Neurovision emails regarding conception and reduction to practice—Exhibit 2017 to Patentee's Preliminary Response to Petition for Inter Partes Review dated Oct. 20, 2016 (140 pages).
Decision; *Medtronic Xomed, Inc. v. Neurovision Medical Products, Inc.*; PTAB Case IPR2016-01847; for U.S. Pat. No. 8,467,844 entered Mar. 23, 2017 (37 pages).
Korean Final Office Action for 10-2012-7011251 dated Jun. 28, 2017 (7 pages).

(56) References Cited

OTHER PUBLICATIONS

Final Office Action for U.S. Appl. No. 13/343,283 dated Jul. 11, 2017 (24 pages).
Japanese 1st Office Action for 2016-502632 dated Jul. 7, 2017 (8 pages).
Final Office Action for U.S. Appl. No. 15/219,726 dated Aug. 2, 2017 (10 pages).
Australian 1st Examination Report for Application No. 2014236572, dated Aug. 10, 2017 (4 pgs).
Non-Final Office Action for U.S. Appl. No. 13/826,323 dated Sep. 8, 2014 (9 pages).
Non-Final Office Action for U.S. Appl. No. 13/826,323 dated Dec. 15, 2014 (11 pages).
Final Office Action for U.S. Appl. No. 13/826,323 dated Mar. 23, 2015 (6 pages).
Advisory Action for U.S. Appl. No. 13/826,323 dated May 28, 2015 (3 pages).
Examiner's Answer for U.S. Appl. No. 13/826,323 dated Nov. 18, 2015 (6 pages).
Notice of Allowance for U.S. Appl. No. 13/826,323 dated Jun. 7, 2017 (5 pages).
International Search Report and Written Opinion, PCT/US2012/069253, dated Feb. 28, 2013 (4 pages).
European Examination Report for Application No. 12818693.9 dated Oct. 25, 2017 (7 pages).
European Office Action for Application No. 14720826.8, dated Jul. 17, 2017 (6 pages).
International Search Report and Written Opinion, PCT/US2014/027810, dated Jul. 25, 2014 (18 pages).
"Applications of High-Pressure Balloons in the Medical Device Industry", 1999 Advanced Polymers, Inc. 1999, Mark A. Saab, President (19 pages).
Canadian 2nd Examiner's Report for 2775588 dated Sep. 5, 2017 (4 pages).
Notice of Allowance for U.S. Appl. No. 14/716,351 dated Sep. 27, 2017 (11 pages).
Advisory Action for U.S. Appl. No. 15/217,572 dated Sep. 29, 2017 (4 pages).
Notice of Allowance for U.S. Appl. No. 15/217,572 dated Nov. 3, 2017 (10 pages).
Notice of Allowance for U.S. Appl. No. 13/343,283 dated Oct. 12, 2017 (12 pages).
Corrected Notice of Allowability for U.S. Appl. No. 13/343,283 dated Nov. 1, 2017 (15 pages).
Australian 3rd Examination Report for 2012363699 dated Sep. 5, 2017 (3 pages).
European Office Action for Application No. 13812262.7, dated Aug. 2, 2017 (8 pages).
Notice of Allowance for U.S. Appl. No. 15/219,726 dated Oct. 2, 2017 (8 pages).
Notice of Allowance for U.S. Appl. No. 13/826,323 dated Sep. 12, 2017 (45 pages).
Notice of Allowance for U.S. Appl. No. 15/899,441 dated Jun. 6, 2018 (8 pages).
European Examination Report for Application No. 14182496.1, dated Oct. 24, 2017 (5 pages).
Canada 1st Examiner's Report for 2860422 dated May 28, 2018 (4 pages).
Chinese 1st Office Action for 201380071314.4 dated Aug. 23, 2018 (17 pages).
Japanese Final (2nd) Office Action for 2016-502632 dated Feb. 21, 2018 (3 pages).

* cited by examiner

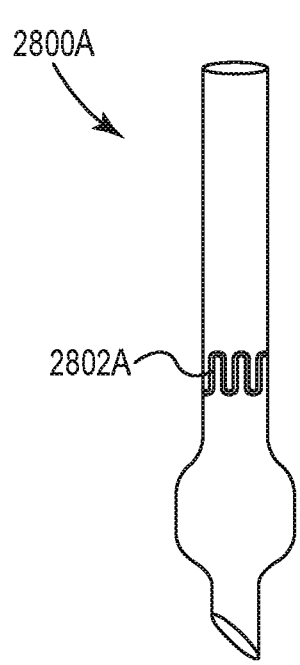 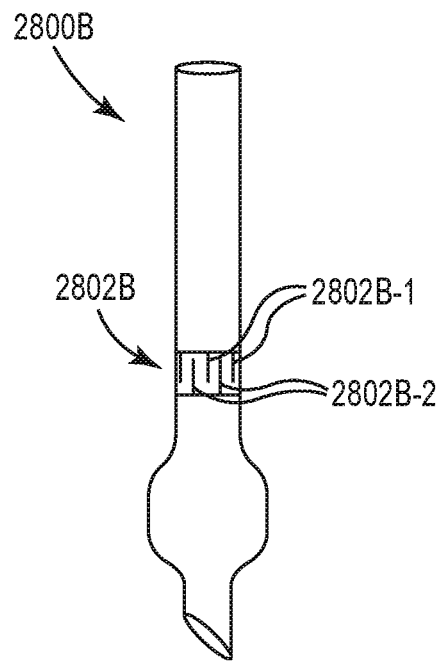
Fig. 28A    Fig. 28B
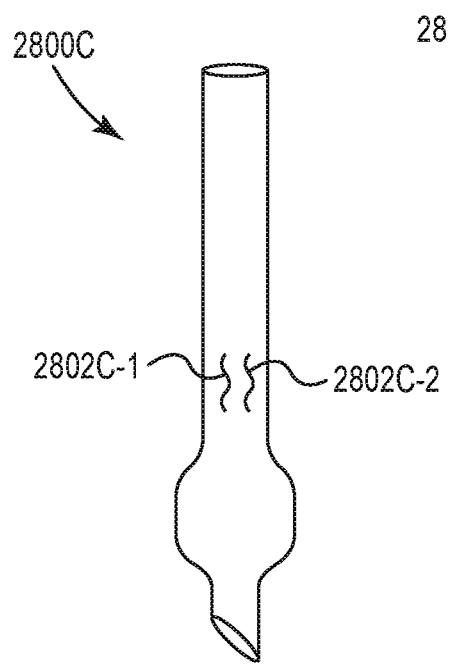 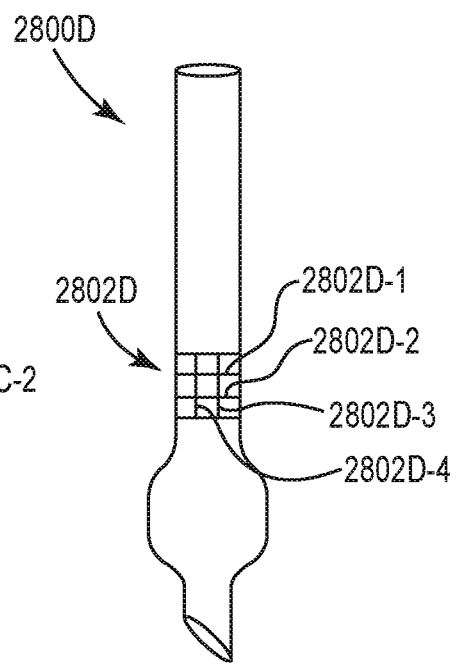
Fig. 28C    Fig. 28D

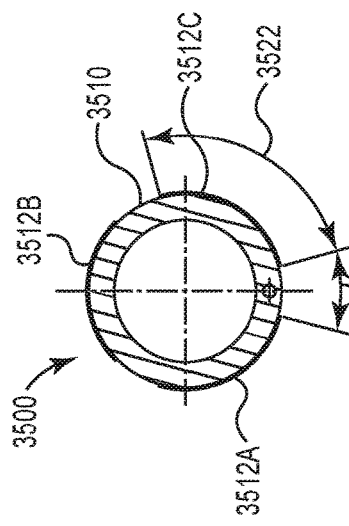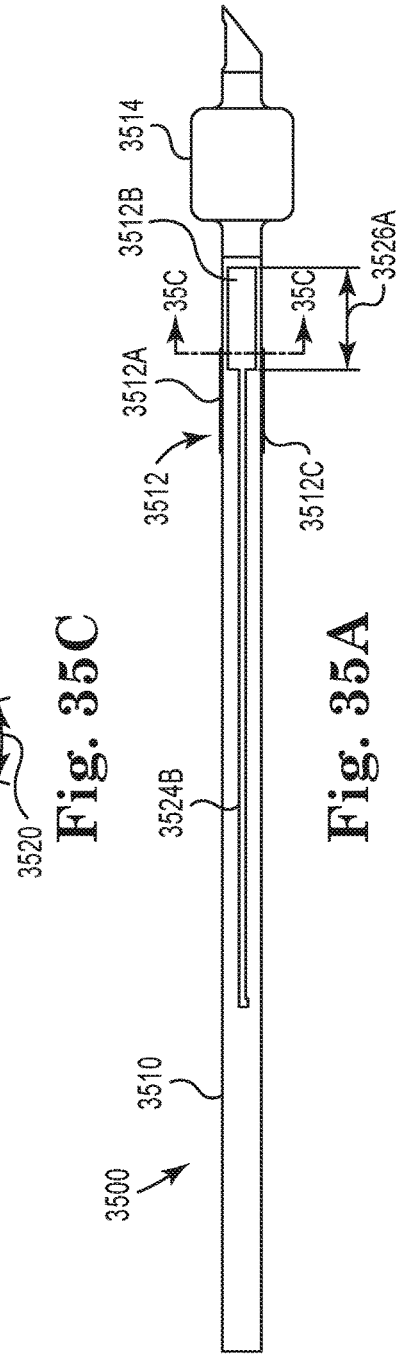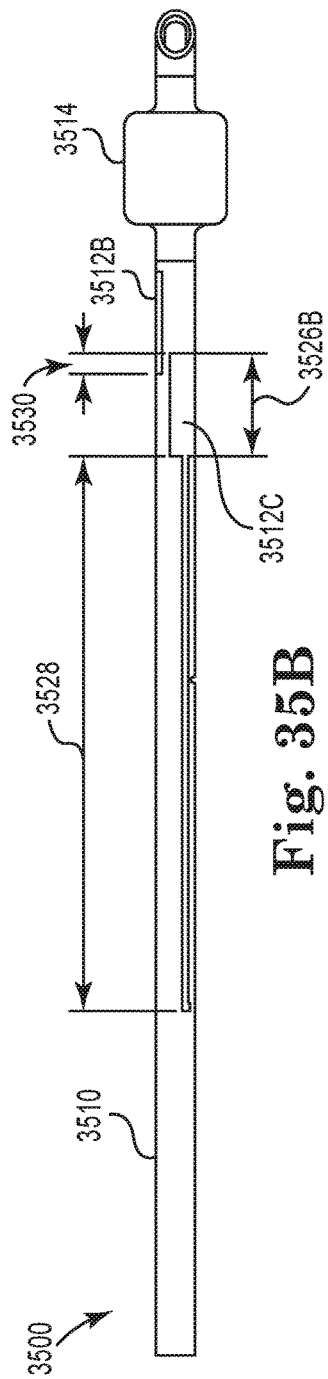
Fig. 35C
Fig. 35A
Fig. 35B

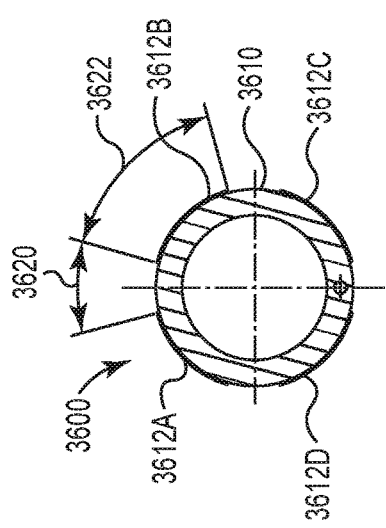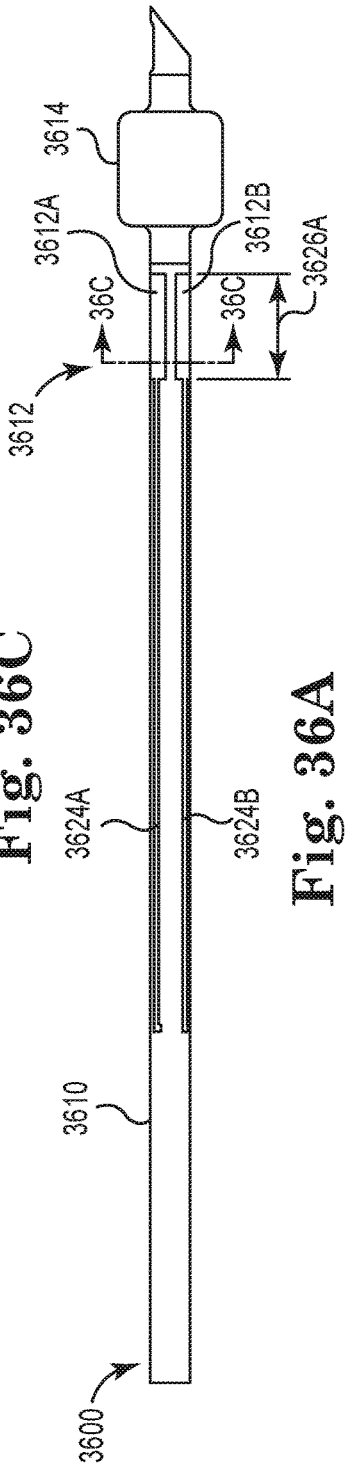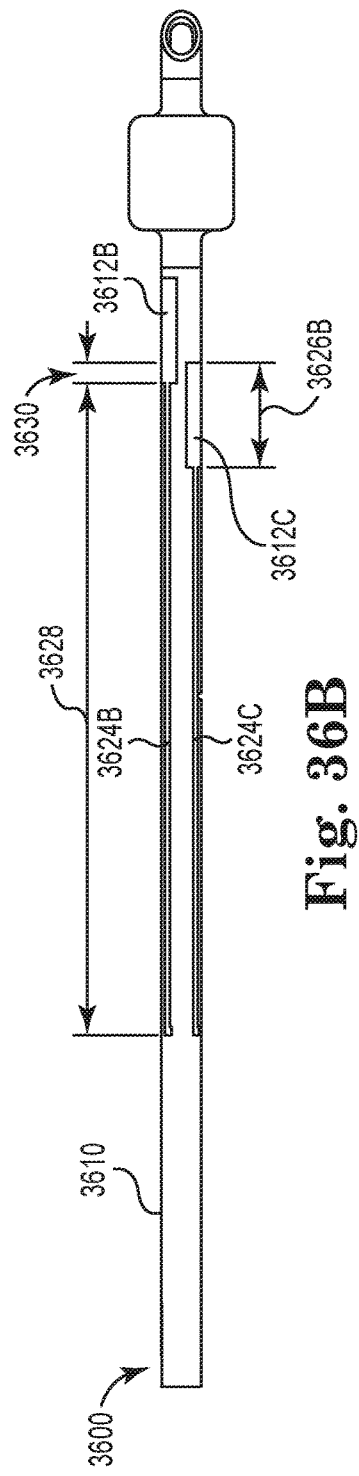

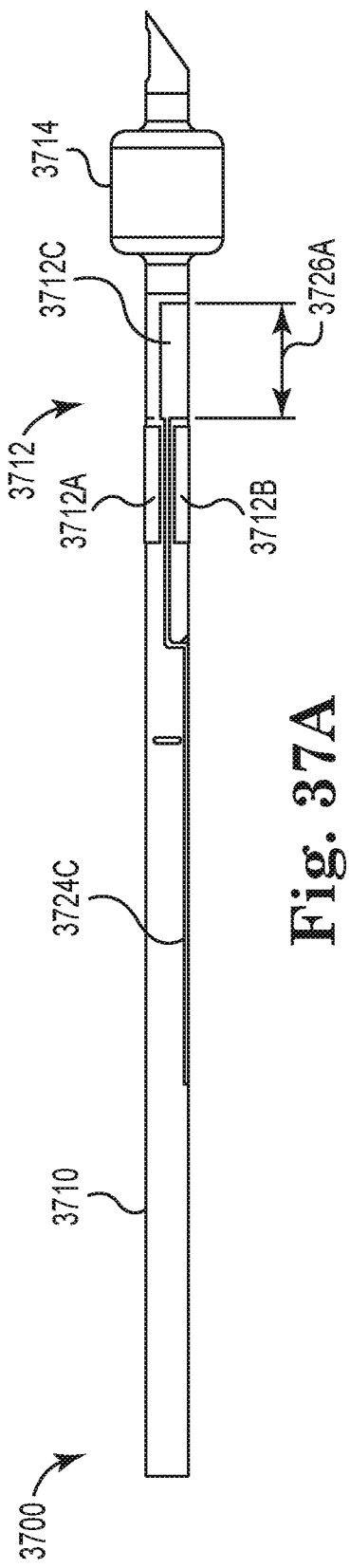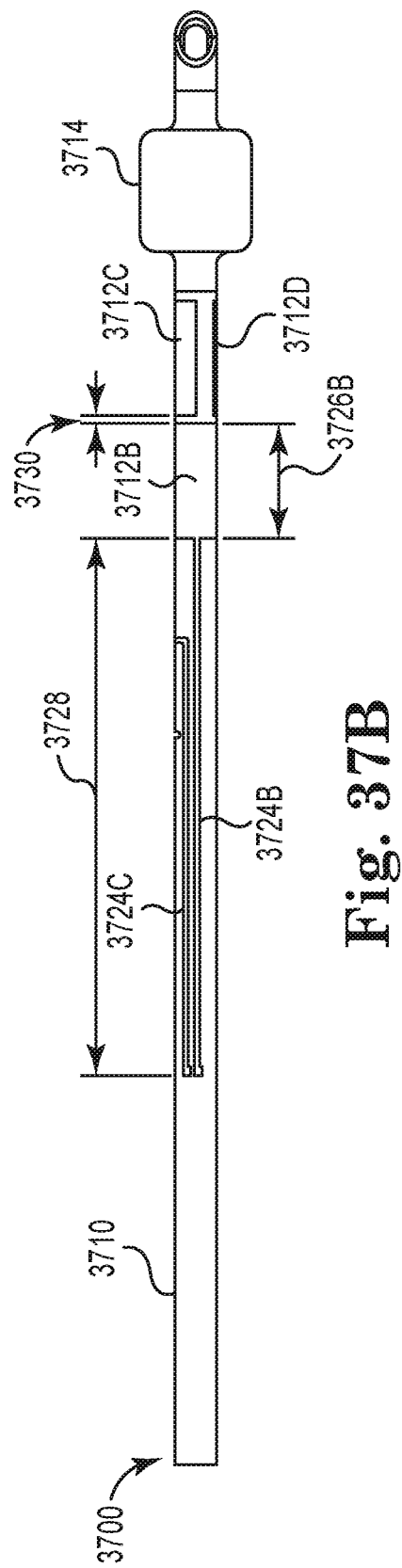

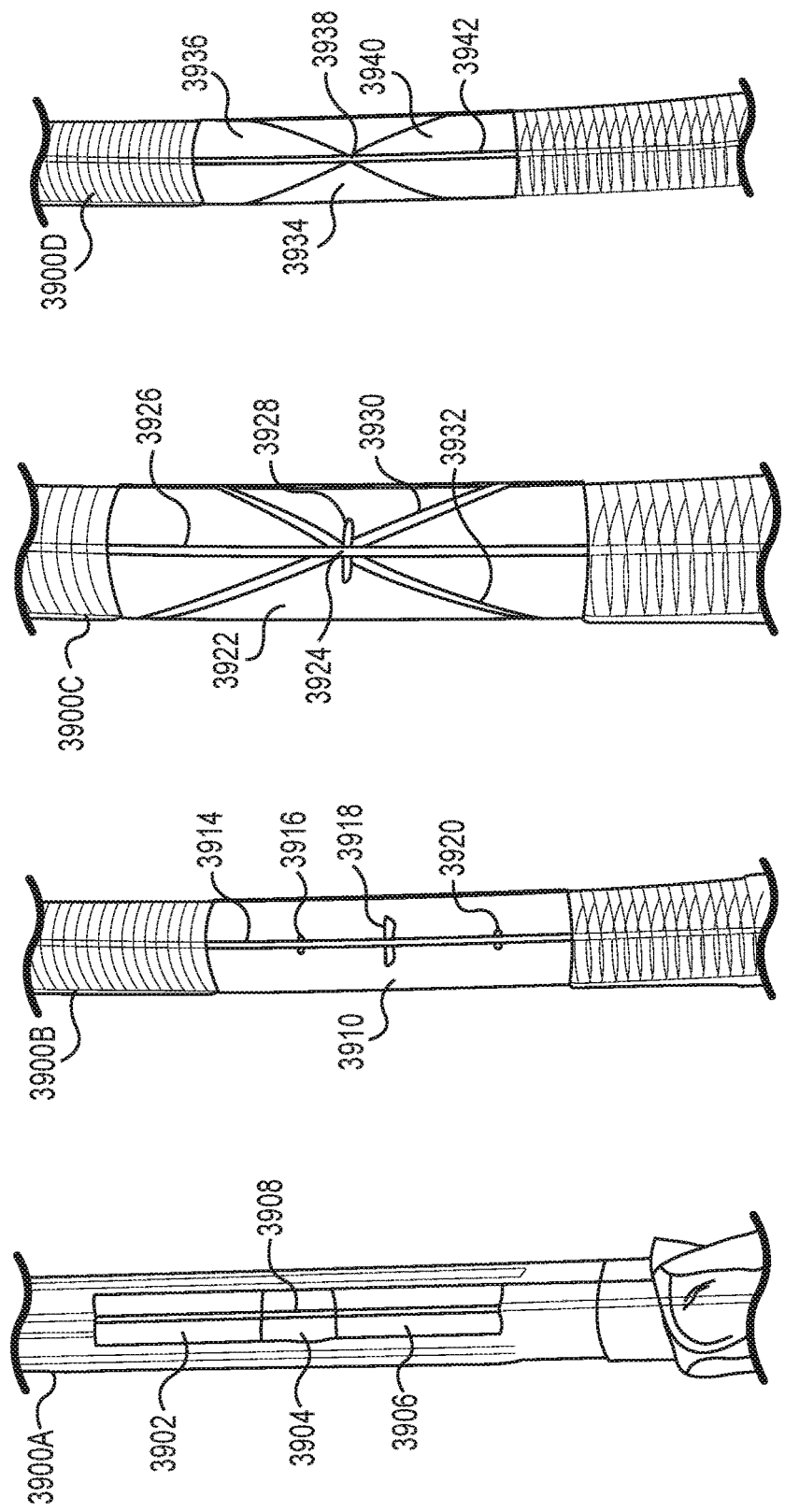

ENDOTRACHEAL TUBE APPARATUS

CROSS-REFERENCE TO RELATED APPLICATIONS

This application is a continuation of U.S. patent application Ser. No. 14/716,351, filed May 19, 2015, entitled "Endotracheal Tube Apparatus", and which is a continuation of U.S. patent application Ser. No. 12/896,578, filed Oct. 1, 2010, entitled "Endotracheal Tube Apparatus", and now U.S. Pat. No. 9,037,226, which claims priority under 35 U.S.C. § 119(e)(1) to U.S. Provisional Patent Application Ser. No. 61/248,294, filed Oct. 2, 2009, entitled "Endotracheal Tube Apparatus", and the entire teachings of which are incorporated herein by reference.

BACKGROUND

Endotracheal tubes include electrodes that are designed to make contact with a patient's vocal cords to facilitate electromyographic (EMG) monitoring of the vocal cords during surgery when connected to an EMG monitoring device. Endotracheal tubes provide an open airway for patient ventilation, and provide for monitoring of EMG activity of the intrinsic laryngeal musculature when connected to an appropriate EMG monitor. Endotracheal tubes can provide continuous monitoring of the nerves supplying the laryngeal musculature during surgical procedures.

SUMMARY

One embodiment is directed to an apparatus for monitoring EMG signals of a patient's laryngeal muscles. The apparatus includes an endotracheal tube having an exterior surface. Conductive ink electrodes are formed on the exterior surface of the endotracheal tube. The conductive ink electrodes are configured to receive the EMG signals from the laryngeal muscles when the endotracheal tube is placed in a trachea of the patient. At least one conductor is coupled to the conductive ink electrodes and is configured to carry the EMG signals received by the conductive ink electrodes to a processing apparatus.

BRIEF DESCRIPTION OF THE DRAWINGS

FIGS. 28A-28D show an EMG endotracheal tube with electrodes having an increased surface area according to various embodiments.

FIG. 35A shows a first side view (posterior side) of an EMG endotracheal tube with three electrodes according to one embodiment.

FIG. 35B shows a second side view (rotated 90 degrees from the view shown in FIG. 35A) of the EMG endotracheal tube shown in FIG. 35A according to one embodiment.

FIG. 35C is a diagram illustrating a cross-sectional view of the endotracheal tube shown in FIGS. 35A and 35B according to one embodiment.

FIG. 36A shows a first side view (posterior side) of an EMG endotracheal tube with four electrodes according to one embodiment.

FIG. 36B shows a second side view (rotated 90 degrees from the view shown in FIG. 36A) of the EMG endotracheal tube shown in FIG. 36A according to one embodiment.

FIG. 36C is a diagram illustrating a cross-sectional view of the endotracheal tube shown in FIGS. 36A and 36B according to one embodiment.

FIG. 37A shows a first side view (posterior side) of an EMG endotracheal tube with four electrodes according to another embodiment.

FIG. 37B shows a second side view (rotated 90 degrees from the view shown in FIG. 37A) of the EMG endotracheal tube shown in FIG. 37A according to one embodiment.

FIGS. 39A-39E show EMG endotracheal tubes with tube placement markings according to various embodiments.

DETAILED DESCRIPTION

Figure 1:
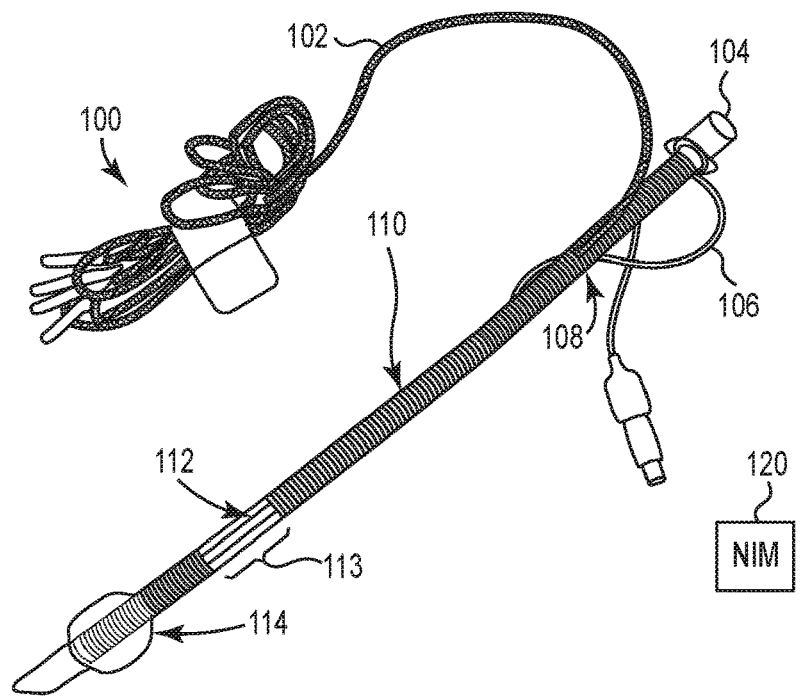
FIG. 1 shows an EMG endotracheal tube made from extruded polymer according to one embodiment.
Figure 2:
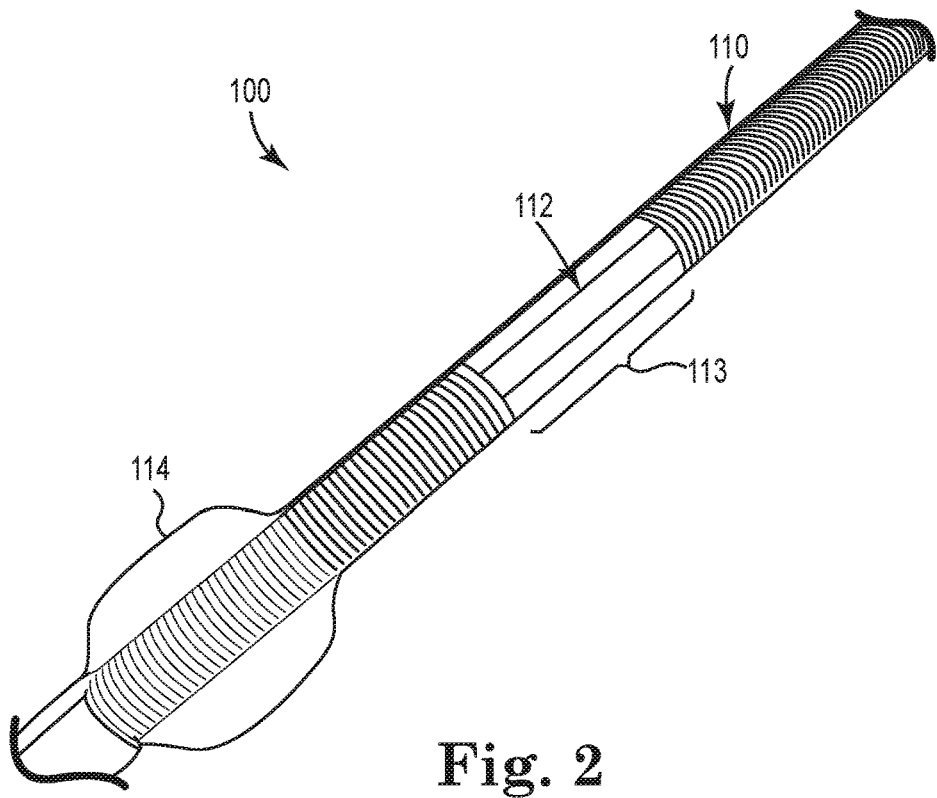
FIG. 2 shows a close-up view of a portion of the endotracheal tube shown in FIG. 1 according to one embodiment.

FIG. 1 shows an EMG endotracheal tube 100 made from extruded polymer. FIG. 2 shows a close-up view of a portion of the endotracheal tube 100 shown in FIG. 1. Endotracheal tube 100 includes solid wires 102, fitting 104, cuff inflating conduit 106, extruded polymer tube 110, wire electrodes 112, and primary cuff 114. Solid wires 102 are connected to wire electrodes 112 at interconnection 108. Tube 110 transports gases to and from the lungs. Fitting 104 is configured to be connected to a respirating machine (not shown) for injecting air into the lungs and withdrawing air from the lungs. Cuff inflating conduit 106 is configured to be connected to a source of compressed air (not shown) for inflating cuff 114. Cuff inflating conduit 106 communicates with a lumen located in the wall of tube 110, and the lumen communicates with primary cuff 114. After endotracheal tube 100 is inserted into the trachea of a patient, electrode wires 112 sense EMG signals, which are output to an EMG processing machine, such as nerve integrity monitor (NIM) device 120, via solid wires 102. Die cut tape may be used to tape tube 110 to a patient's mouth to secure the tube and keep it appropriately positioned.

In one embodiment, the NIM 120 is configured to determine when the electrodes 112 are in contact with the vocal folds, and is configured to provide an alert to the surgeon when such contact is lost. In one embodiment, the NIM 120 is also configured to determine whether the electrodes 112 are in contact with muscle or tissue based on the received signals. In one embodiment, EMG tube 100 is configured to wirelessly communicate with the NIM 120, and the NIM 120 is configured to wirelessly monitor the electrodes 112. In form of this embodiment, the NIM 120 wirelessly transmits energy to the electrodes 112, and the electrodes 112 wirelessly transmit EMG signals to the NIM 120.

Some existing endotracheal tubes can rotate, which causes the electrodes to move away from the vocal folds. In contrast, tube 110 includes a flexible tube segment 113 that is configured to make contact with the vocal folds, and exposed electrodes 112 are formed over the flexible tube segment 113. The flexible tube segment 113 is more flexible or softer (e.g., made from a low durometer material) than the remainder of the tube 110, which allows the electrodes 112 to maintain better opposition with the vocal folds and reduce or eliminate translational and rotational movement of the tube 110. In one embodiment, primary cuff 114 is formed from a tacky, low-durometer material to contour against the tracheal rings, which helps to reduce or eliminate translational and rotational movement of the tube 110. In one embodiment, electrodes 112 are about 1.3 inches long. In another embodiment, electrodes 112 are about 1.9 inches long. Extending the length of electrodes 112 helps the tube 110 to become less sensitive to neck extension.

In one embodiment, tube 110 is a braided tube that is more flexible than conventional solid polymer tubes, and that reduces kinking. Tube 110 according to one embodiment is formed from a braided polymer or nitinol within a thin-walled tube, and reduces or eliminates rotation of the tube at the vocal folds, while allowing a proximal portion of the tube to rotate.

Figure 3:
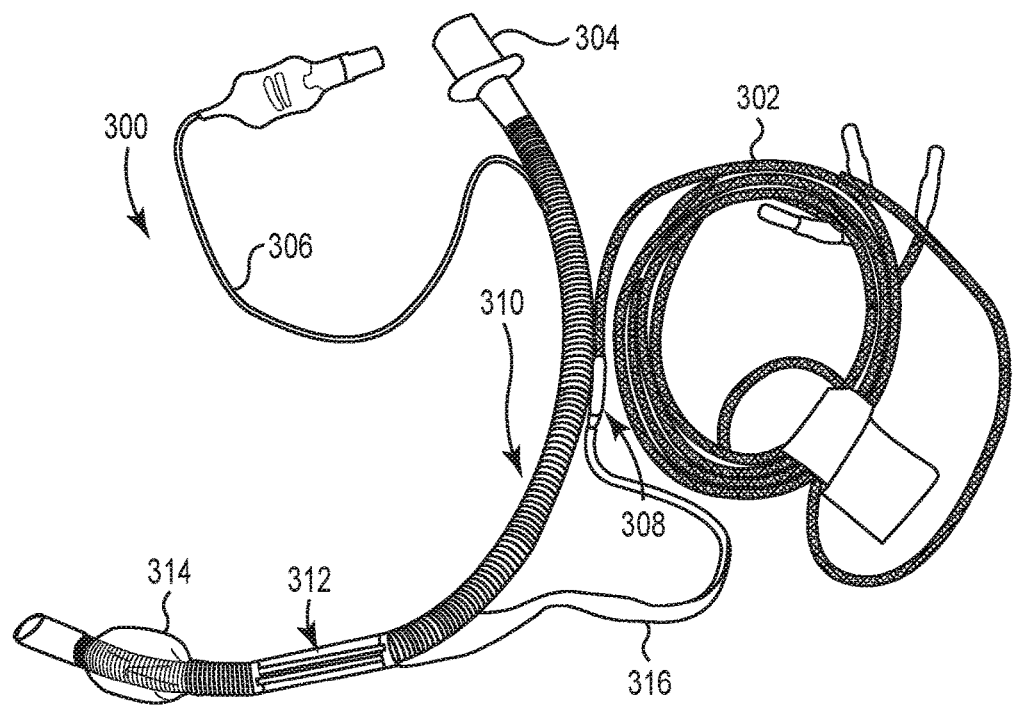
FIG. 3 shows an EMG endotracheal tube made from PVC according to one embodiment.
Figure 4:
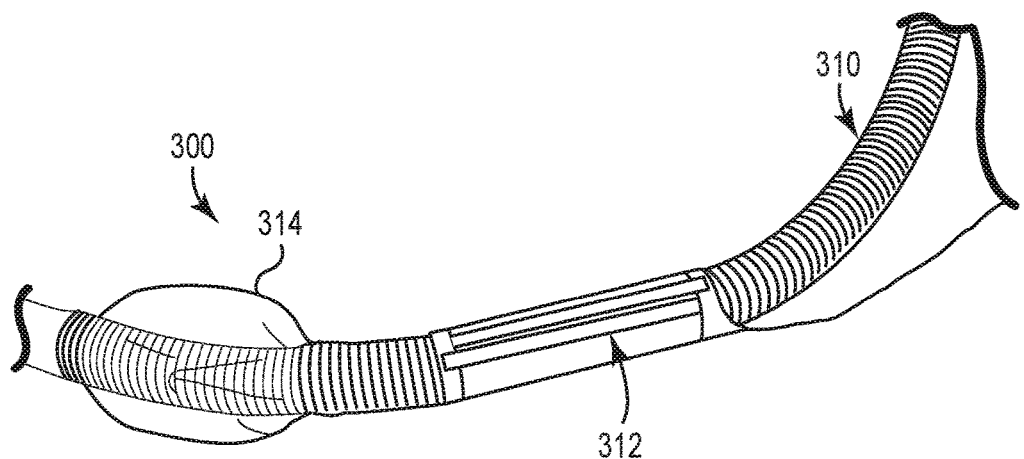
FIG. 4 shows a close-up view of a portion of the endotracheal tube shown in FIG. 3 according to one embodiment.

FIG. 3 shows an EMG endotracheal tube 300 made from PVC. FIG. 4 shows a close-up view of a portion of the endotracheal tube 300 shown in FIG. 3. Endotracheal tube 300 includes solid wires 302, fitting 304, cuff inflating conduit 306, PVC tube 310, taped-on electrodes 312, primary cuff 314, and electrode wires 316. Solid wires 302 are connected to electrode wires 316 at interconnection 308, and electrode wires 316 are connected to taped-on electrodes 312. Tube 310 transports gases to and from the lungs. Fitting 304 is configured to be connected to a respirating machine (not shown) for injecting air into the lungs and withdrawing air from the lungs. Cuff inflating conduit 306 is configured to be connected to a source of compressed air (not shown) for inflating cuff 314. Cuff inflating conduit 306 communicates with a lumen located in the wall of tube 310, and the lumen communicates with primary cuff 314. After endotracheal tube 300 is inserted into the trachea of a patient, taped-on electrodes 312 sense EMG signals, which are output to an EMG processing machine (e.g., NIM device 120) via solid wires 302.

Figure 5:
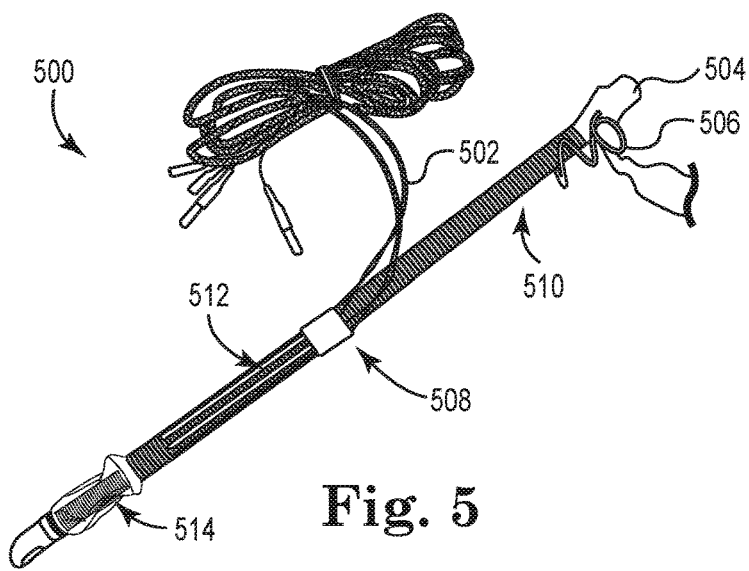
FIG. 5 shows an EMG endotracheal tube with conductive ink electrodes printed on the tube according to one embodiment.
Figure 6:
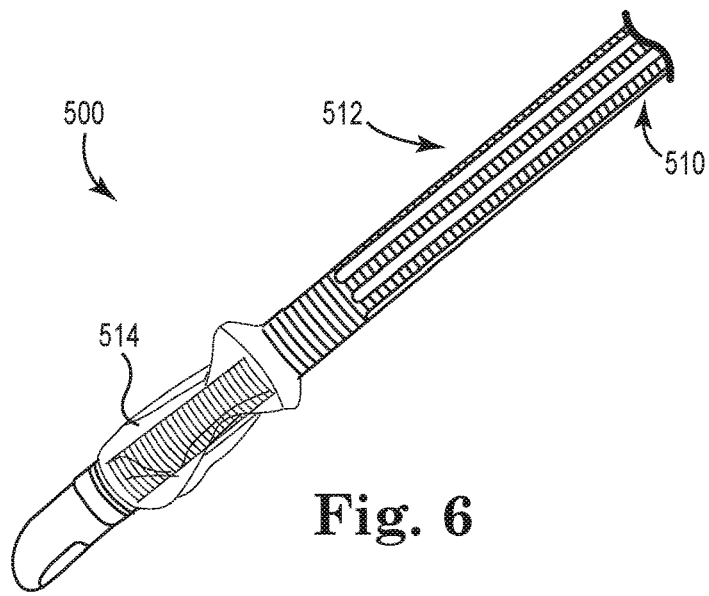
FIG. 6 shows a close-up view of a portion of the endotracheal tube shown in FIG. 5 according to one embodiment.

FIG. 5 shows an EMG endotracheal tube 500 with conductive ink electrodes printed on the tube according to one embodiment. FIG. 6 shows a close-up view of a portion of the endotracheal tube 500 shown in FIG. 5 according to one embodiment. Endotracheal tube 500 includes solid wires 502, fitting 504, cuff inflating conduit 506, PVC tube 510, conductive ink electrodes 512, and primary cuff 514. Solid wires 502 are connected to conductive ink electrodes 512 at interconnection 508. Tube 510 transports gases to and from the lungs. Fitting 504 is configured to be connected to a respirating machine (not shown) for injecting air into the lungs and withdrawing air from the lungs. Cuff inflating conduit 506 is configured to be connected to a source of compressed air (not shown) for inflating cuff 514. Cuff inflating conduit 506 communicates with a lumen 522 (FIG. 7) located in the wall 520 of tube 510, and the lumen 522 communicates with primary cuff 514. After endotracheal tube 500 is inserted into the trachea of a patient, conductive ink electrodes 512 sense EMG signals, which are output to an EMG processing machine (e.g., NIM device 120) via solid wires 502.

Figure 7:
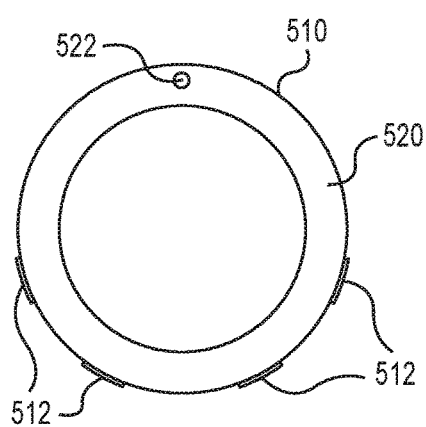
FIG. 7 is a diagram illustrating a cross-sectional view of the endotracheal tube shown in FIG. 5 according to one embodiment.

FIG. 7 is a diagram illustrating a cross-sectional view of the endotracheal tube 500 shown in FIG. 5 according to one embodiment. As shown in FIG. 7, lumen 522 is located in the wall 520 of tube 510 for inflating the cuff 514. Conductive ink electrodes 512 are formed on the outer surface of wall 520. In one embodiment, conductive ink electrodes 512 are formed by tracing or printing a silver filled polymer conductive ink or a carbon conductive ink on tube 510. Conductive inks are available in variety of flowable material choices such as Silver, Carbon, Gold, Platinum, Palladium, Silver-Tungsten, and Silver-Titanium. Conductive inks can be deposited on the substrate using various known technologies such as PAD printing, Screen printing, Ink jet dispensing, digital printing, Micropen dispensing, painting, vapor deposition, and plasma sputtering. Conductive inks can be used both for stimulation and recording purposes in nerve monitoring applications.

Figure 8:
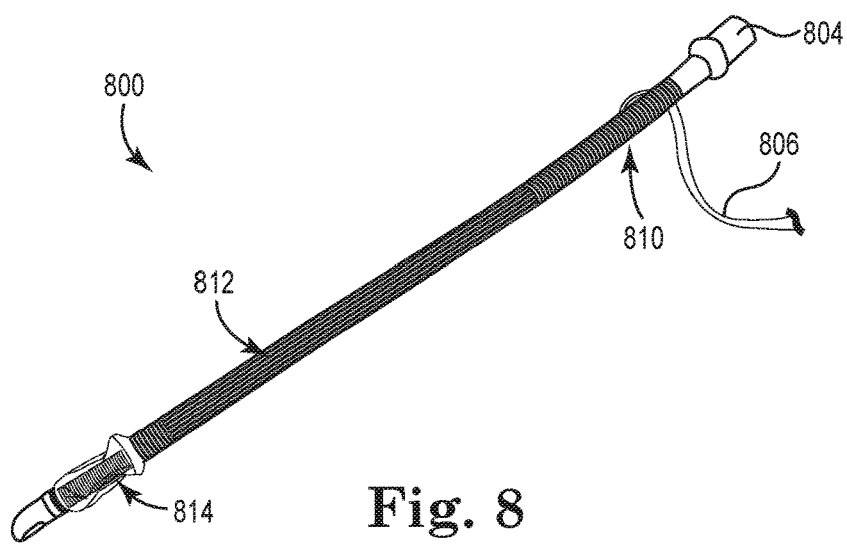
FIG. 8 shows an EMG endotracheal tube with multiple pairs of conductive ink electrodes printed around the circumference of the tube according to one embodiment.
Figure 9:
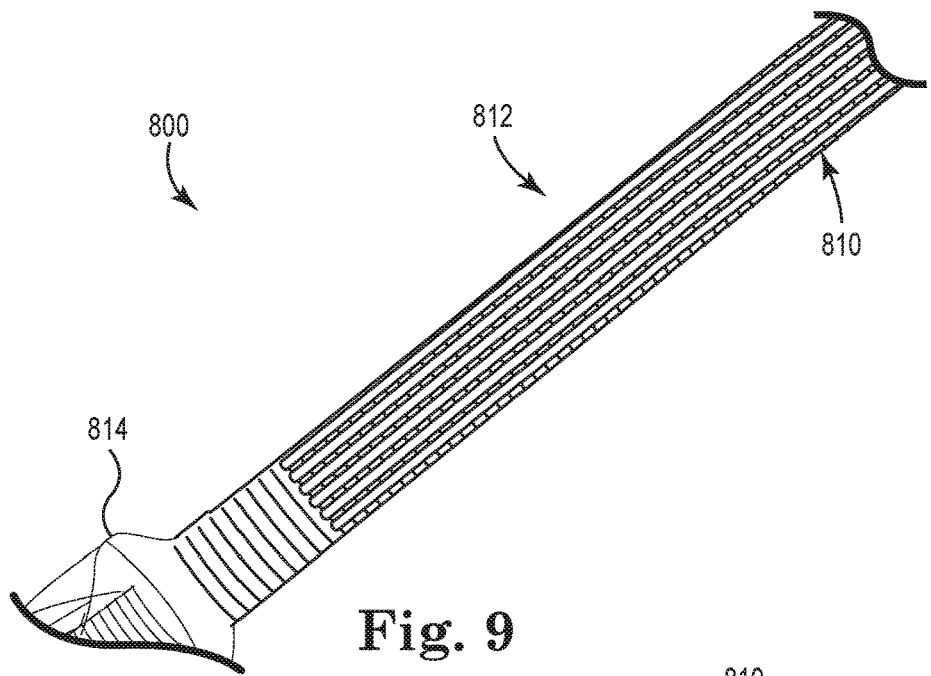
FIG. 9 shows a close-up view of a portion of the endotracheal tube shown in FIG. 8 according to one embodiment.

FIG. 8 shows an EMG endotracheal tube 800 with multiple pairs of conductive ink electrodes printed around the circumference of the tube according to one embodiment. FIG. 9 shows a close-up view of a portion of the endotracheal tube 800 shown in FIG. 8 according to one embodiment. Endotracheal tube 800 includes fitting 804, cuff inflating conduit 806, PVC tube 810, conductive ink electrodes 812, and primary cuff 814. Tube 810 transports gases to and from the lungs. Fitting 804 is configured to be connected to a respirating machine (not shown) for injecting air into the lungs and withdrawing air from the lungs. Cuff inflating conduit 806 is configured to be connected to a source of compressed air (not shown) for inflating cuff 814. Cuff inflating conduit 806 communicates with a lumen 822 (FIG. 10) located in the wall 820 of tube 810, and the lumen 822 communicates with primary cuff 814. After endotracheal tube 800 is inserted into the trachea of a patient, conductive ink electrodes 812 sense EMG signals, which are output to an EMG processing machine (e.g., NIM device 120) via solid wires connected to the electrodes 812 (e.g., solid wires 502 shown in FIG. 5).

Figure 10:
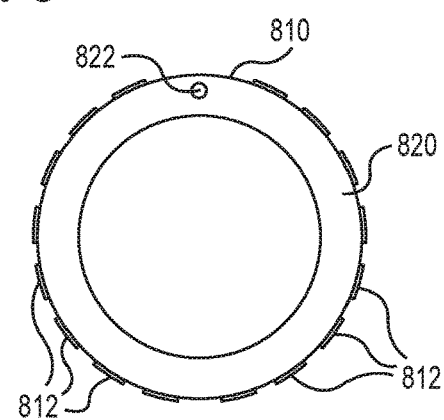
FIG. 10 is a diagram illustrating a cross-sectional view of the endotracheal tube shown in FIG. 8 according to one embodiment.

FIG. 10 is a diagram illustrating a cross-sectional view of the endotracheal tube 800 shown in FIG. 8 according to one embodiment. As shown in FIG. 10, lumen 822 is located in the wall 820 of tube 810 for inflating the cuff 814. Multiple pairs of conductive ink electrodes 812 are formed around the circumference of the tube 810 to achieve uninterrupted EMG recording even when the tube 810 is shifted rotationally. In one embodiment, conductive ink electrodes 812 are formed by tracing or printing a silver filled polymer conductive ink on tube 810.

Figure 11:
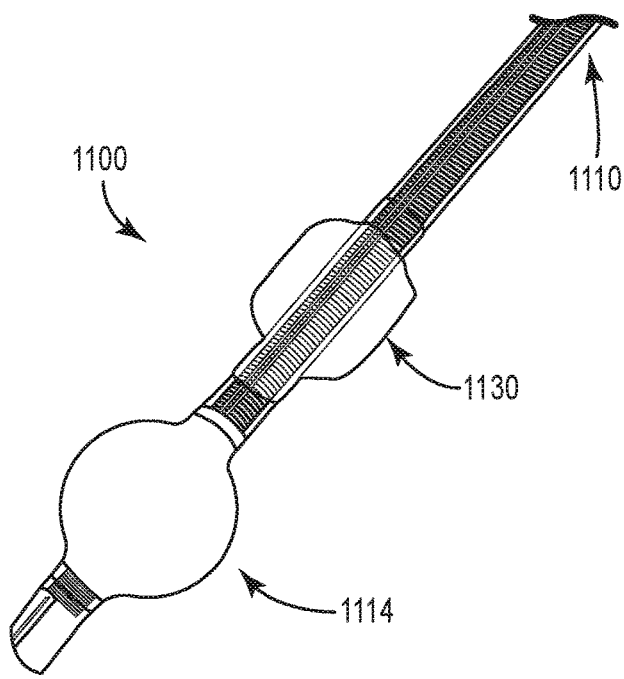
FIG. 11 shows an EMG endotracheal tube with a primary cuff and a secondary cuff according to one embodiment.
Figure 12A:
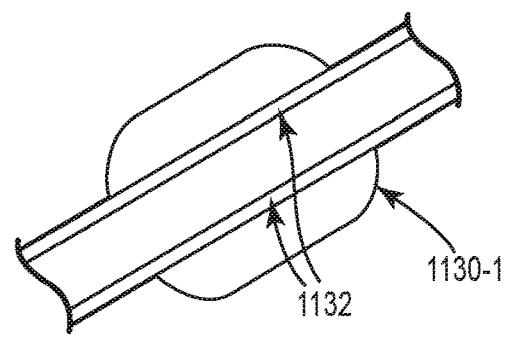
FIG. 12A shows the secondary cuff of the endotracheal tube shown in FIG. 11 with conductive ink electrodes printed on the secondary cuff according to one embodiment.
Figure 12B:
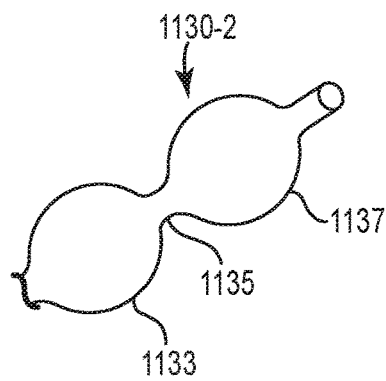
FIG. 12B shows the secondary cuff of the endotracheal tube shown in FIG. 11 according to another embodiment.

FIG. 11 shows an EMG endotracheal tube 1100 with a primary cuff 1114 and a secondary cuff 1130 according to one embodiment. FIG. 12A shows a close-up view of the secondary cuff 1130 of the endotracheal tube shown in FIG. 11 with conductive ink electrodes 1132 printed on the secondary cuff 1130 according to one embodiment. FIG. 12B shows a close-up view of the secondary cuff 1130 of the endotracheal tube shown in FIG. 11 according to another embodiment. The embodiment of the secondary cuff 1130 shown in FIG. 12A is identified by reference number 1130-1, and the embodiment shown in FIG. 12B is identified by reference number 1130-2. Endotracheal tube 1100 includes PVC tube 1110, primary cuff 1114, and secondary cuff 1130 with conductive ink electrodes 1132 formed thereon. Tube 1110 transports gases to and from the lungs. At least one cuff inflating conduit (not shown) is configured to be connected to a source of compressed air (not shown) for inflating cuffs 1114 and 1130. After endotracheal tube 1100 is inserted into the trachea of a patient, the secondary cuff 1130 is inflated and the conductive ink electrodes 1132 come in contact with the vocal folds and sense EMG signals from the vocal folds. The sensed signals are output to an EMG processing machine (e.g., NIM device 120) via wires connected to the electrodes 1132. In one embodiment, the secondary cuff 1130 is made of a compliant or semi-compliant material, and conductive ink electrodes 1132 are formed by tracing or printing a silver filled polymer conductive ink on secondary cuff 1130. The secondary cuff 1130 with the silver ink printed thereon helps establish a better electrode contact when inflated over the vocal folds. Electrodes 1132 may be sprayed on secondary cuff 1130 or tube 1110, and may cover substantially the entire surface of secondary cuff 1130. Electrodes 1132 may take a variety of shapes or forms other than that shown in FIG. 12A, such as any of the shapes or forms shown in any of the other Figures of the present disclosure, or other shapes. In other embodiments, EMG tube 1100 may include three or more cuffs.

Secondary cuff 1130 may also have a different shape than that shown in FIG. 12A, such as that shown in FIG. 12B. As shown in FIG. 12B, secondary cuff 1130-2 has a flattened peanut shape with two rounded ends 1133 and 1137 that taper to a mid portion 1135. The flattened peanut shape of the cuff 1130-2 according to one embodiment fits or contours to the shape of the vocal folds, and helps to reduce or eliminate translational and rotational movement of the tube 1110. In another embodiment, the secondary cuff 1130 is formed from an elastomer or foam pillow with two rounded ends that taper to a mid portion like that shown in FIG. 12B. In one form of this embodiment, the ends of the pillow have a substantially triangular cross-section. In one embodiment, the secondary cuff 1130 includes one or more position sensors to monitor the position or location of the tube 1110.

Figure 13:
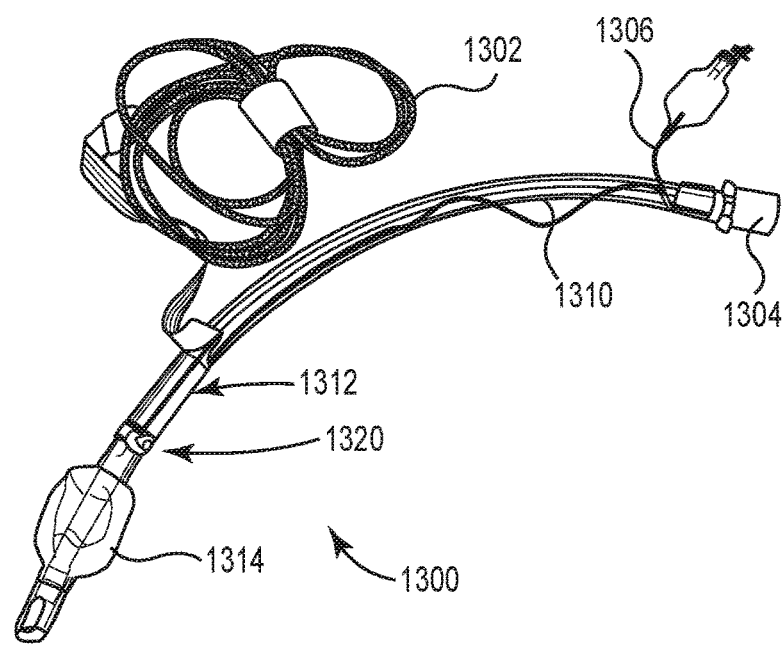
FIG. 13 shows an EMG endotracheal tube with a visual indicator for tracking and verifying electrode location according to one embodiment.
Figure 14:
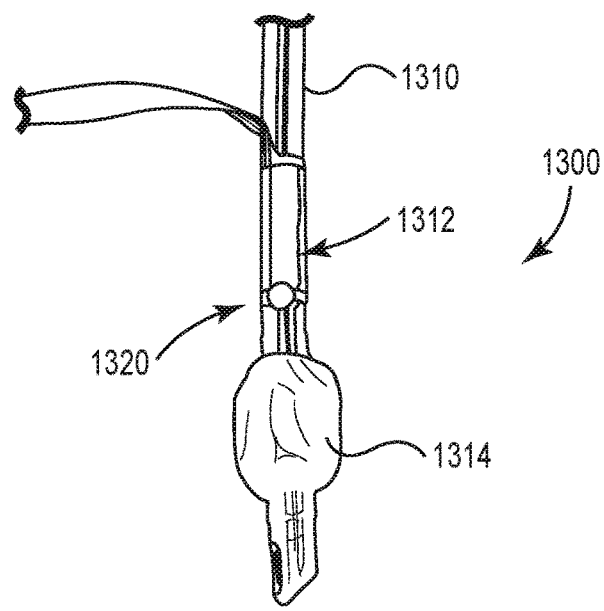
FIG. 14 shows a close-up view of a portion of the endotracheal tube shown in FIG. 13 according to one embodiment.

FIG. 13 shows an EMG endotracheal tube 1300 with a visual indicator 1320 for tracking and verifying electrode location according to one embodiment. FIG. 14 shows a close-up view of a portion of the endotracheal tube 1300 shown in FIG. 13 according to one embodiment. Endotracheal tube 1300 includes solid wires 1302, fitting 1304, cuff inflating conduit 1306, PVC tube 1310, electrodes 1312, primary cuff 1314, and visual indicator 1320. Solid wires 1302 are connected to electrodes 1312. Tube 1310 transports gases to and from the lungs. Fitting 1304 is configured to be connected to a respirating machine (not shown) for injecting air into the lungs and withdrawing air from the lungs. Cuff inflating conduit 1306 is configured to be connected to a source of compressed air (not shown) for inflating cuff 1314. Cuff inflating conduit 1306 communicates with a lumen located in the wall of tube 1310, and the lumen communicates with primary cuff 1314. After endotracheal tube 1300 is inserted into the trachea of a patient, electrodes 1312 sense EMG signals, which are output to an EMG processing machine (e.g., NIM device 120) via solid wires 1302.

In one embodiment, visual indicator 1320 is a bright lit light emitting diode (LED) or fiber optic light source that is used to track and verify the location of the electrodes 1312. The visual indicator 1320 is placed on the surface of the tube 1310 near the electrodes 1312 to identify the electrode position with respect to the vocal fold after tube intubation. A user can see the light spot facing anterior and mark the spot on the patient's skin. In another embodiment, visual indicator 1320 is an LED band that surrounds a portion or the entire circumference of tube 1310.

Figure 15:
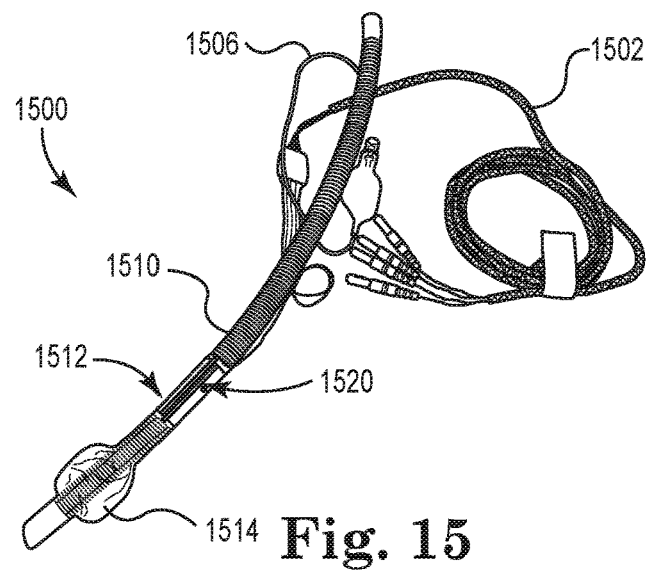
FIG. 15 shows an EMG endotracheal tube with a magnet indicator for tracking and verifying electrode location according to one embodiment.
Figure 16:
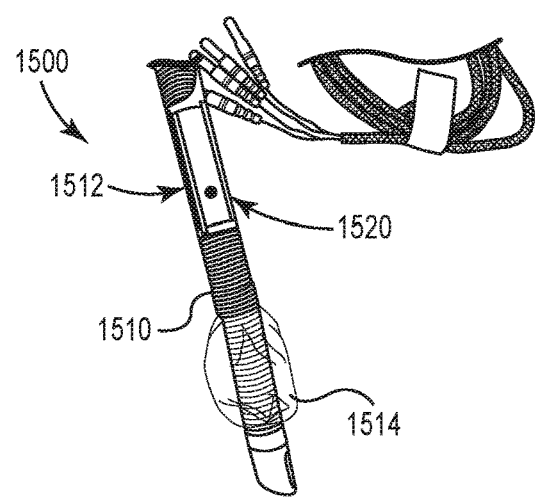
FIGS. 16 and 17 show close-up views of a portion of the endotracheal tube shown in FIG. 15 according to one embodiment.
Figure 17:
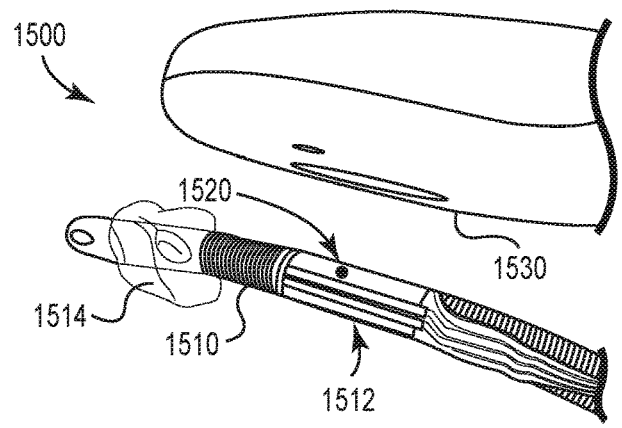

FIG. 15 shows an EMG endotracheal tube 1500 with a magnet indicator 1520 for tracking and verifying electrode location according to one embodiment. FIGS. 16 and 17 show close-up views of a portion of the endotracheal tube 1500 shown in FIG. 15 according to one embodiment. Endotracheal tube 1500 includes solid wires 1502, cuff inflating conduit 1506, tube 1510, electrodes 1512, primary cuff 1514, and magnetic indicator 1520. Solid wires 1502 are connected to electrodes 1512. Tube 1510 transports gases to and from the lungs. A fitting of the tube 1500 is configured to be connected to a respirating machine (not shown) for injecting air into the lungs and withdrawing air from the lungs. Cuff inflating conduit 1506 is configured to be connected to a source of compressed air (not shown) for inflating cuff 1514. Cuff inflating conduit 1506 communicates with a lumen located in the wall of tube 1510, and the lumen communicates with primary cuff 1514. After endotracheal tube 1500 is inserted into the trachea of a patient, electrodes 1512 sense EMG signals, which are output to an EMG processing machine (e.g., NIM device 120) via solid wires 1502.

In one embodiment, magnetic indicator 1520 is a tiny magnet that is used to track and verify the location of the electrodes 1512. The magnetic indicator 1520 is placed on the surface of the tube 1510 near the electrodes 1512 to identify the electrode position with respect to the vocal fold after tube intubation. A user can track and locate the magnet inside the patient with a device 1530 (FIG. 17) that includes a magnet pick-up sensor.

In addition to the LED-based and magnet-based techniques described above with respect to FIGS. 13-17, other embodiments may use other techniques for determining electrode location within a patient, such as the following: (1) locating an anatomy landmark; (2) Automatic Periodic Stimulation (APS) electrode tracking; (3) sonar/ultra sound (similar to a wall stud finder); (4) surgical navigation using a coil; (5) use of stimulator combined with locating device, and synchronizing the lighting of LED with the stimulator pulse of the wand; (6) use of an accelerometer (e.g., positioned on the cuff) to monitor movement; (7) use of a vibration sensor and air inlets and outlets so that air flow past the vocal folds causes vibration that is sensed by the vibration sensor; (8) use of an ultrasonic transducer in or on the tube, and a sensing circuit external to the body; (9) use of a resonant circuit for positional and rotational sensing (could use stimulator channel to provide pulses); use resonant vibration near vocal fold tissue resonance; mechanical impedance of the vocal fold is detected by impedance match and energy transfer to surrounding tissue; use surface acoustic wave or other mechanical resonator; (10) use of a pressure sensor or pressure sensor array near the electrode sites to detect engagement with the vocal folds (e.g., a pressure sensitive surface with capacitive sensor on each side of the tube); (11) wireless sensors linked to a wireless interface (e.g., the tube may include a wireless video chip to send signals to an external monitor (e.g., picture-in-picture on the NIM or miniscreen) to view placement in real time); (12) temperature sensors (temperature will be higher when in contact with the vocal folds); (13) embedded fiber optic viewer with light source at proximal end and viewing window near electrodes (software in NIM to identify position); (14) one or more RF ID tags incorporated in or on the tube with signals sent to an external device or the NIM for reading and evaluation; (15) flexible piezo strips for monitoring the movement of one or more portions of the tube, such as the flexible tube segment 113 (FIGS. 1 and 2)—monitoring movement of the flexible tube segment 113 indirectly results in monitoring of the movement of the vocal folds; (16) impedance monitors placed around one or more portions of the tube, such as around tube segment 113 (FIGS. 1 and 2), to detect changes in the diameter of the tube at the vocal folds (such impedance monitoring allows the vocal fold movement to be monitored without recording EMG potentials); and (17) use electrodes with the ability to differentiate between muscle contact and non-muscle contact, which helps the NIM to ensure proper position and contact.

Figure 18:
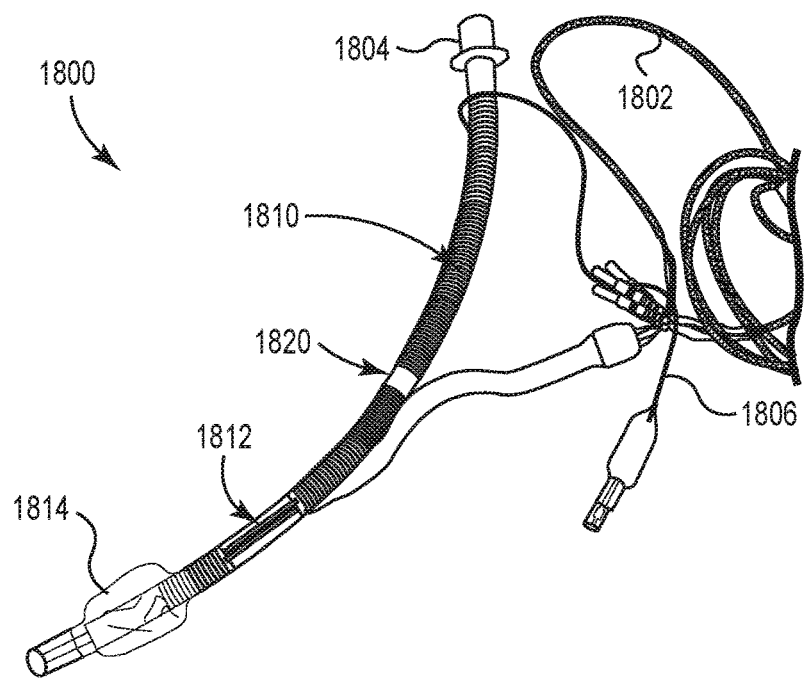
FIG. 18 shows an EMG endotracheal tube with a coupling adapter to provide rotational freedom according to one embodiment.
Figure 19:
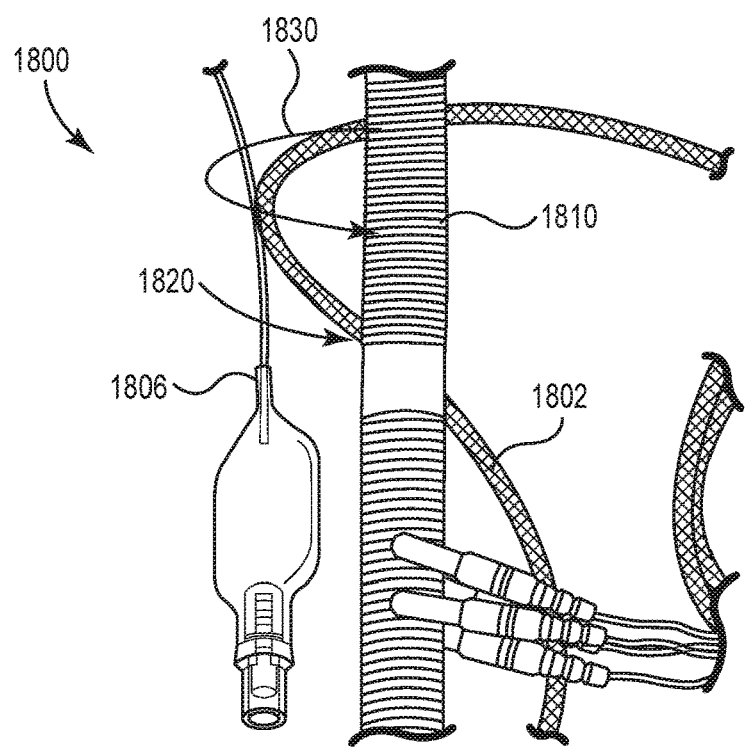
FIG. 19 shows a close-up view of a portion of the endotracheal tube shown in FIG. 18 according to one embodiment.

FIG. 18 shows an EMG endotracheal tube 1800 with a coupling adapter 1820 to provide rotational freedom according to one embodiment. FIG. 19 shows a close-up view of a portion of the endotracheal tube 1800 shown in FIG. 18 according to one embodiment. Endotracheal tube 1800 includes solid wires 1802, fitting 1804, cuff inflating conduit 1806, PVC tube 1810, electrodes 1812, primary cuff 1814, and plastic coupling adapter 1820. Solid wires 1802 are connected to electrodes 1812. Tube 1810 transports gases to and from the lungs. Fitting 1804 is configured to be connected to a respirating machine (not shown) for injecting air into the lungs and withdrawing air from the lungs. Cuff inflating conduit 1806 is configured to be connected to a source of compressed air (not shown) for inflating cuff 1814. Cuff inflating conduit 1806 communicates with a lumen located in the wall of tube 1810, and the lumen communicates with primary cuff 1814. After endotracheal tube 1800 is inserted into the trachea of a patient, electrodes 1812 sense EMG signals, which are output to an EMG processing machine (e.g., NIM device 120) via solid wires 1802.

In one embodiment, after insertion of the endotracheal tube 1800 into a patient, the tube is taped to the patient's mouth. The coupling adapter 1820 is positioned at the proximal end (away from the patient's mouth), and allows the proximal end of the tube 1810 to swivel around as indicated by arrow 1830 in FIG. 19, which minimizes rotational movement of the distal portion of the tube 1810 in the patient. In one embodiment, the coupling adapter 1820 allows thirty degrees of rotation in either direction. In another embodiment, endotracheal tube 1800 includes a tube within a tube configuration that allows a proximal portion of the tube to rotate while preventing rotation of the distal portion of the tube. In one embodiment, primary cuff 1814 is formed from a sticky or tacky material (e.g., a tacky balloon) to help prevent the distal portion of the tube from rotating.

Figure 20:
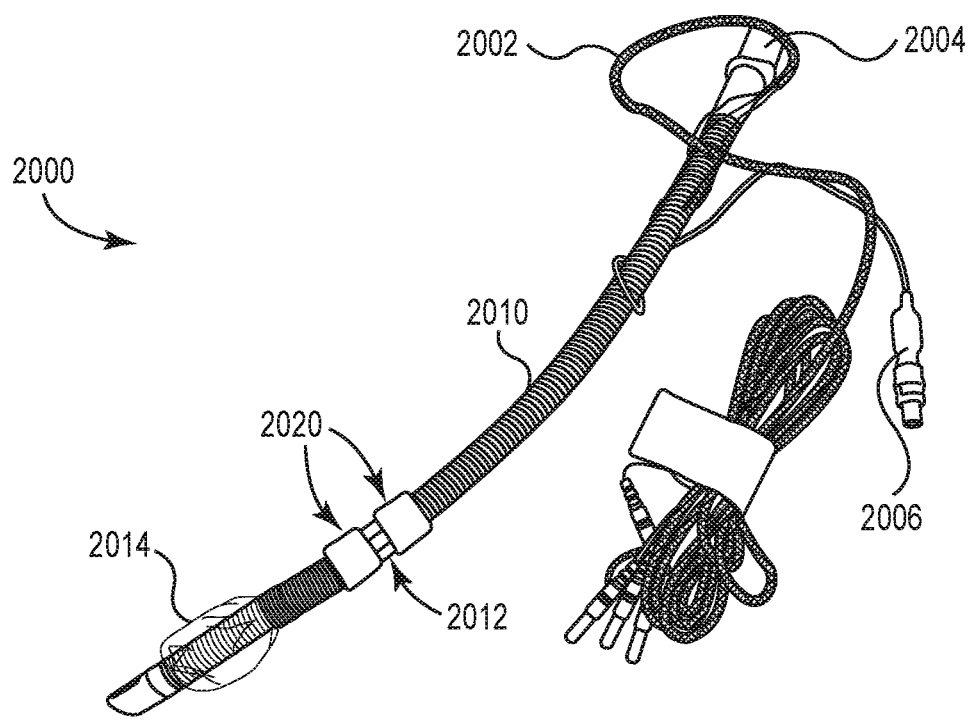
FIG. 20 shows an EMG endotracheal tube with ribs on the top and bottom of the EMG electrodes according to one embodiment.
Figure 21:
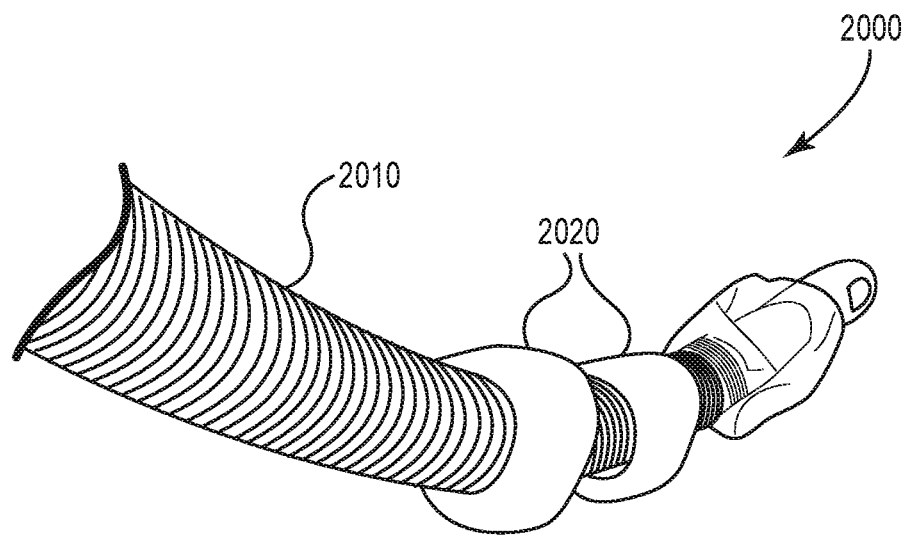
FIG. 21 shows a close-up view of a portion of the endotracheal tube shown in FIG. 20 according to one embodiment.

FIG. 20 shows an EMG endotracheal tube 2000 with ribs 2020 on the top and bottom of the EMG electrodes 2012 according to one embodiment. FIG. 21 shows a close-up view of a portion of the endotracheal tube 2000 shown in FIG. 20 according to one embodiment. Endotracheal tube 2000 includes solid wires 2002, fitting 2004, cuff inflating conduit 2006, tube 2010, electrodes 2012, primary cuff 2014, and ribs 2020. Solid wires 2002 are connected to electrodes 2012. Tube 2010 transports gases to and from the lungs. Fitting 2004 is configured to be connected to a respirating machine (not shown) for injecting air into the lungs and withdrawing air from the lungs. Cuff inflating conduit 2006 is configured to be connected to a source of compressed air (not shown) for inflating cuff 2014. Cuff inflating conduit 2006 communicates with a lumen located in the wall of tube 2010, and the lumen communicates with primary cuff 2014. After endotracheal tube 2000 is inserted into the trachea of a patient, electrodes 2012 sense EMG signals, which are output to an EMG processing machine (e.g., NIM device 120) via solid wires 2002.

The ribs 2020 according to one embodiment provide a positive feel when passing the vocal fold during intubation, and the ribs 2020 on top and bottom of the vocal fold will not allow the tube 2010 to move out of position. In one embodiment, the ribs 2020 are shaped to match the contour of the opening, and are made with compliant or semi-compliant material. In another embodiment, ribs 2020 are implemented with inflatable balloons.

Figure 22:
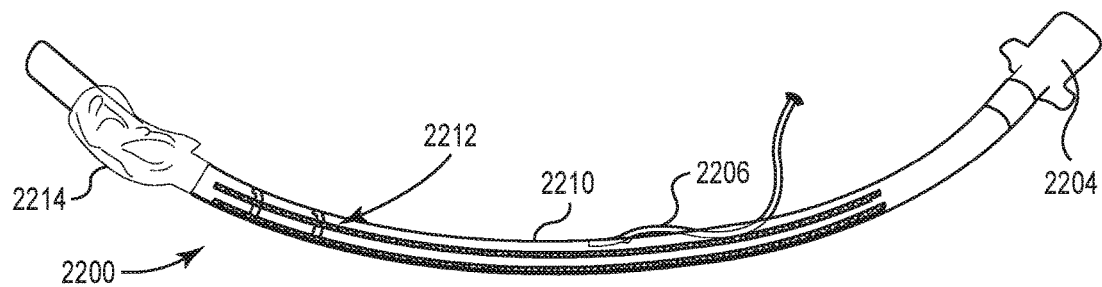
FIG. 22 shows an EMG endotracheal tube with conductive tape on the surface of the tube for recording EMG signals according to one embodiment.
Figure 23:
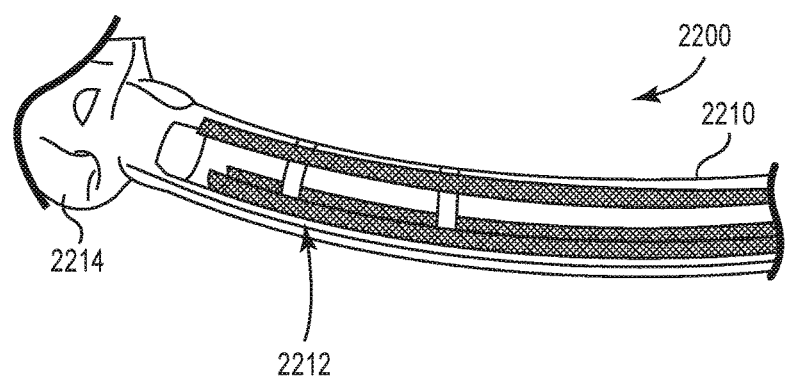
FIG. 23 shows a close-up view of a portion of the endotracheal tube shown in FIG. 22 according to one embodiment.

FIG. 22 shows an EMG endotracheal tube 2200 with conductive tape on the surface of the tube for recording EMG signals according to one embodiment. FIG. 23 shows a close-up view of a portion of the endotracheal tube 2200 shown in FIG. 22 according to one embodiment. Endotracheal tube 2200 includes fitting 2204, cuff inflating conduit 2206, tube 2210, electrodes 2212, and primary cuff 2214. Solid wires are connected to electrodes 2212. Tube 2210 transports gases to and from the lungs. Fitting 2204 is configured to be connected to a respirating machine (not shown) for injecting air into the lungs and withdrawing air from the lungs. Cuff inflating conduit 2206 is configured to be connected to a source of compressed air (not shown) for inflating cuff 2214. Cuff inflating conduit 2206 communicates with a lumen located in the wall of tube 2210, and the lumen communicates with primary cuff 2214. After endotracheal tube 2200 is inserted into the trachea of a patient, electrodes 2212 sense EMG signals, which are output to an EMG processing machine (e.g., NIM device 120) via solid wires attached to the electrodes 2212.

In the embodiment illustrated in FIGS. 22 and 23, electrodes 2212 are strips of conducting tape that stick to the surface of the tube 2210. In one embodiment, the conducting tape is a woven material, and replaces the solid wire electrodes found in some conventional tubes (2 channel or multiple pairs). In one embodiment, one or more of the strips 2212 shown in FIGS. 22 and 23 comprise a piezo strip for monitoring movement of the tube 2210. In another embodiment, electrodes 2212 are covered with an expandable, conductive foam that expands when it absorbs moisture, thereby providing improved contact with the vocal folds.

Figure 25:
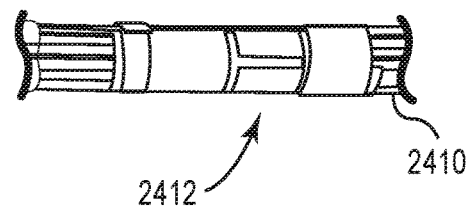
FIGS. 25 and 26 show close-up views of a portion of the endotracheal tube shown in FIG. 24 according to one embodiment.
Figure 24:
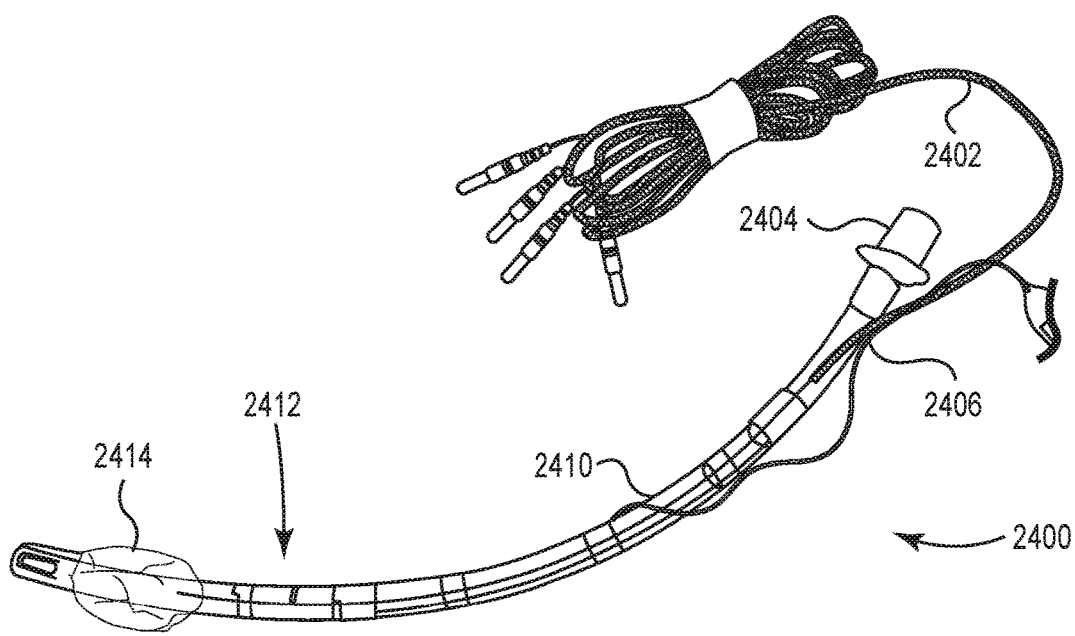
FIG. 24 shows an EMG endotracheal tube with a custom extruded PVC tube according to one embodiment.
Figure 26:
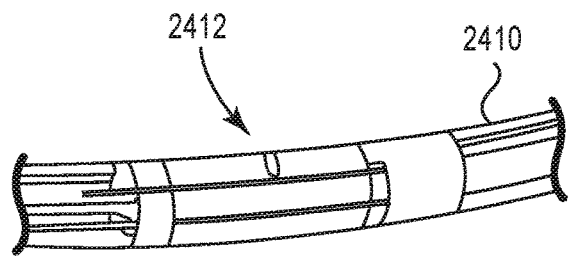

FIG. 24 shows an EMG endotracheal tube 2400 with a custom extruded PVC tube according to one embodiment. FIGS. 25 and 26 show close-up views of a portion of the endotracheal tube 2400 shown in FIG. 24 according to one embodiment. Endotracheal tube 2400 includes solid wires 2402, fitting 2404, cuff inflating conduit 2406, tube 2410, electrodes 2412, and primary cuff 2414. Solid wires 2402 are connected to electrodes 2412. Tube 2410 transports gases to and from the lungs. Fitting 2404 is configured to be connected to a respirating machine (not shown) for injecting air into the lungs and withdrawing air from the lungs. Cuff inflating conduit 2406 is configured to be connected to a source of compressed air (not shown) for inflating cuff 2414. Cuff inflating conduit 2406 communicates with a lumen located in the wall of tube 2410, and the lumen communicates with primary cuff 2414. After endotracheal tube 2400 is inserted into the trachea of a patient, electrodes 2412 sense EMG signals, which are output to an EMG processing machine (e.g., NIM device 120) via solid wires 2402.

In one embodiment, tube 2410 comprises a custom extruded PVC tube (rigid or reinforced), and the PVC cuff is not sticky like a silicone cuff. The size of the custom extruded PVC tube 2410 according to one embodiment is close to standard off-the-shelf endotracheal tubes.

Features of embodiments of the EMG endotracheal tubes described herein include: (1) more placement tolerant than conventional tubes; (2) NIM is used to help place the tube; (3) the electrode is periodically checked to assure constant contact; (4) intentional bend in correct direction for proper tube insertion; (5) include high brightness LED in tube to observe placement through the skin; (6) use external Hall sensors with magnets in the tube to sense correct tube placement; (7) kit-pack tapes for stabilizing the tube; (8) improved means to detect EMG generators and shunt tissue; (9) use muscle "artifact" as an indicator of proper placement (artifact can be minimized by adjusting tube position); (10) fiber optic bundle connected to light source or camera; (11) a "fixture" molded at the proximal end of the tube to register on the patient anatomy for proper orientation; (12) improved way and connector for plugging into the patient box; (13) creation of 4-channels from 2-channels via added connectors (not added wires) or cross-point switch within the NIM; (14) providing a signal from the NIM to measure resistance and phase angle of tissue contacting the electrodes to decide if there is enough EMG generator tissue vs. shunt tissue; (15) EMG tube with reduced overall outer diameter; and (16) reduced cost and quality associated issues with custom extruded silicone tubing by utilizing standard off the shelf endotracheal tube. Additional features and information are set forth below.

The EMG tube electrodes according to one embodiment may contact both EMG generators (striated muscle) and shunt tissue (conductive tissue that does not generate EMG signals but which does conduct current, thus shunting (reducing) the EMG signal available for the amplifier). A "high quality tube placement" has a high ratio of EMG generator tissue to shunt tissue.

Embodiments of the EMG endotracheal tubes described herein may include a conducting hydro gel coating on the electrodes, such as electrodes 112 (FIG. 1). Coating the electrodes with a conducting hydro gel increases the contact surface of the electrodes, allows for more rotation of the EMG tube without a loss of contact with the vocal folds, and results in an improved recorded signal. Some embodiments may use paddle electrodes for posterior and anterior monitoring, including monitoring arytenoids and posterior cricoarytenoid (PCA).

There are some problems with existing EMG endotracheal, such as: (1) ridges on the outside of the tube can cause tissue irritation; (2) the tube can shift rotationally during surgery; and (3) the tube wall is too thick. These problems are addressed in one embodiment in the following ways: (1) use of a non-silicone material such as pebax with Teflon for the tube, which allows the tube to slide easily (a high friction material may be used for the cuff to help prevent translational shift); (2) placing bumps for wires on the inner diameter (ID) of the tube; (3) splicing together different pieces of tubing along the length (each with potentially a different cross-sectional shape) to get a more optimal cross-sectional geometry that more closely matches a patient's anatomy, such as using a first tube portion near the proximal end with a circular cross-section to allow rotation and a second tube portion near the vocal folds with a triangular cross-section (e.g., with a circular or triangular inner diameter); (4) just above the electrodes, adding a region of lower wall thickness to de-couple upper sections from lower section; and (5) decoupling the proximal end of the tube from the distal end by switching to a braided tube from a spring coil reinforced tube.

Figure 27:
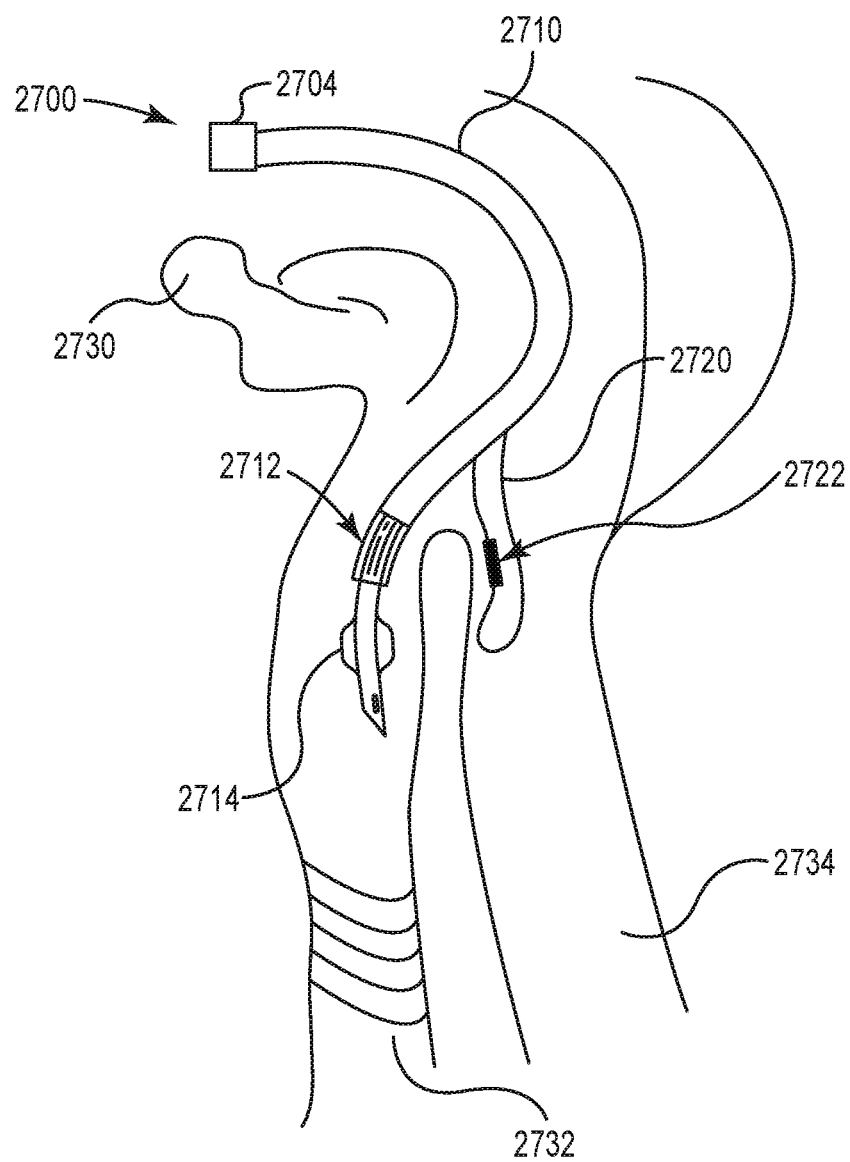
FIG. 27 shows an EMG endotracheal tube positioned within a patient's throat according to one embodiment.

FIG. 27 shows an EMG endotracheal tube 2700 positioned within a patient's throat according to one embodiment. Endotracheal tube 2700 includes fitting 2704, tube 2710, electrodes 2712, primary cuff 2714, esophageal extension 2720, and esophageal electrodes 2722. The portions of the patient's anatomy shown in FIG. 27 include tongue 2730, trachea 2732, and esophagus 2734. Tube 2710 transports gases to and from the lungs. Fitting 2704 is configured to be connected to a respirating machine (not shown) for injecting air into the lungs and withdrawing air from the lungs. A cuff inflating conduit is configured to be connected to a source of compressed air for inflating cuff 2714. After endotracheal tube 2700 is inserted into the trachea 2732 of the patient, electrodes 2712 sense EMG signals, which are output to an EMG processing machine (e.g., NIM device 120) via solid wires connected to electrodes 2712.

As shown in FIG. 27, esophageal extension 2720 extends away from the tube 2710 and into the patient's esophagus 2734. The esophageal electrodes 2722 formed on the extension 2720 sense signals from the backside muscles of the vocal folds from the esophagus 2734. The electrodes 2722 according to one embodiment are used to record EMG signals of laryngeal muscles behind the larynx. In one embodiment, the electrodes 2722 are positioned behind the cricoid cartilage during surgery. Most of the muscles innervated by the recurrent laryngeal nerve (RLN) are behind and posterolateral to the larynx (e.g., arytenoids, posterior cricoarytenoid (PCA), and lateral cricoarytenoid (LCA)). Positioning the electrodes 2722 behind the cricoid cartilage provides superior EMG signals. In one embodiment, esophageal extension 2720 is also used to set both the depth of insertion of the tube 2710 and the angular placement.

FIG. 28A shows an EMG endotracheal tube 2800A with electrodes having an increased surface area according to one embodiment. Tube 2800A includes electrode 2802A, which has a sinusoidal wave shape that extends around the circumference of the tube 2800A with peaks and valleys that extend in a longitudinal direction of the tube 2800A.

FIG. 28B shows an EMG endotracheal tube 2800B with electrodes having an increased surface area according to another embodiment. Tube 2800B includes electrodes 2802B, which are formed around a circumference of the tube 2800B and extend in a longitudinal direction of the tube 2800B. Electrodes 2802B include a first set of electrodes 2802B-1 that are interleaved with and longitudinally displaced from a second set of electrodes 2802B-2. The electrodes 2802B-1 are positioned closer to a proximal end of the tube 2800B than electrodes 2802B-2, and the electrodes 2802B-2 are positioned closer to a distal end of the tube 2800B than electrodes 2802B-1.

FIG. 28C shows an EMG endotracheal tube 2800C with electrodes having an increased surface area according to another embodiment. Tube 2800C includes electrodes 2802C-1 and 2802C-2, which each have a sinusoidal wave shape that extends along a portion of the length of the tube 2800C, with peaks and valleys that extend in a lateral direction of the tube 2800C.

FIG. 28D shows an EMG endotracheal tube 2800D with electrodes having an increased surface area according to another embodiment. Tube 2800D includes electrode array 2802D, which includes a plurality of horizontal electrodes 2802D-1 and 2802D-2 and a plurality of vertical electrodes 2802D-3 and 2802D-4 that form a grid pattern. Horizontal electrodes 2802D-1 and 2802D-2 extend laterally around a circumference of the tube 2800D, and vertical electrodes 2802D-3 and 2802D-4 extend longitudinally along a portion of the length of the tube 2800D.

The electrode configurations shown in FIGS. 28A-28D help to reduce or eliminate rotational sensitivity of the tube. In one embodiment, the shape of the electrodes conforms to the vocal folds to avoid shunting problems.

Figure 29:
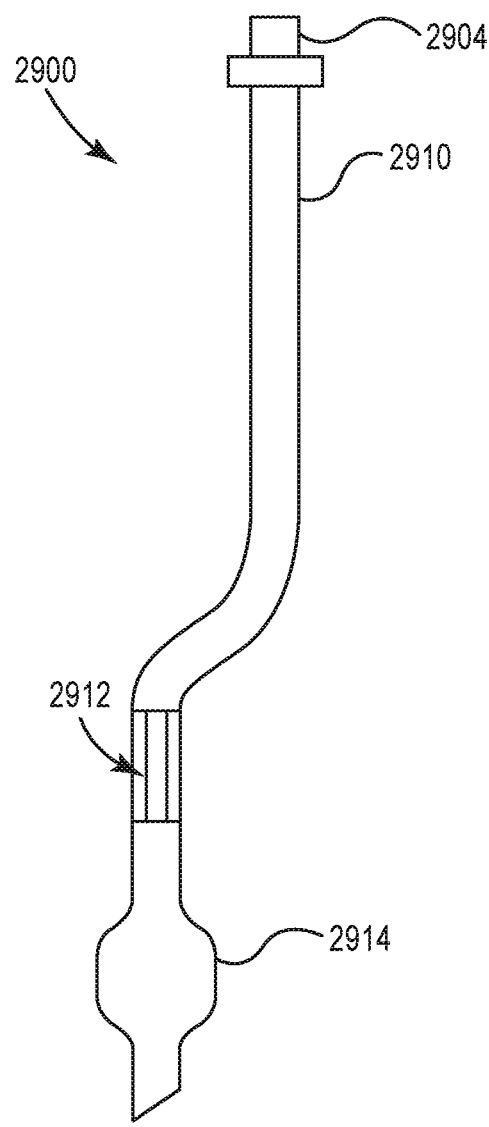
FIG. 29 shows an EMG endotracheal tube with an overall shape that is curved to match the shape of a human throat according to one embodiment.

FIG. 29 shows an EMG endotracheal tube 2900 with an overall shape that is curved to match the shape of a human throat according to one embodiment. Endotracheal tube 2900 includes fitting 2904, tube 2910, electrodes 2912, and primary cuff 2914. Tube 2910 transports gases to and from the lungs. Fitting 2904 is configured to be connected to a respirating machine (not shown) for injecting air into the lungs and withdrawing air from the lungs. A cuff inflating conduit is configured to be connected to a source of compressed air for inflating cuff 2914. After endotracheal tube 2900 is inserted into the trachea of the patient, electrodes 2912 sense EMG signals, which are output to an EMG processing machine (e.g., NIM device 120) via solid wires connected to electrodes 2912.

As shown in FIG. 29, tube 2910 is not a straight tube, but rather is bent or curved in at least one location along the length of the tube 2910, such that the tube 2910 has a natural shape that matches or substantially matches the shape of a human throat. The curved shape of the tube 2910 provides tactual feel for proper placement in a patient.

Figure 30:
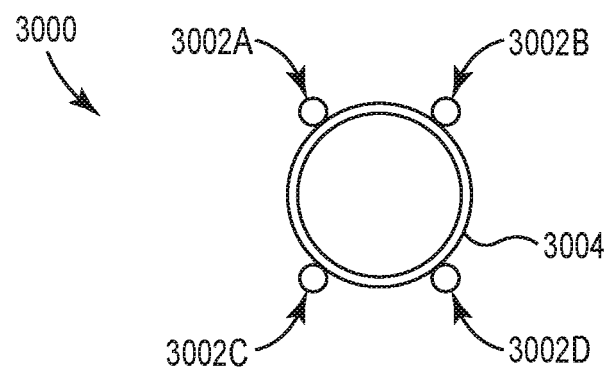
FIG. 30 shows a cross-sectional view of an EMG endotracheal tube with electrodes configured to reduce or eliminate rotational sensitivity according to one embodiment.

FIG. 30 shows a cross-sectional view of an EMG endotracheal tube 3000 with electrodes configured to reduce or eliminate rotational sensitivity according to one embodiment. Four electrodes 3002A-3002D are positioned on tube 3004 and extend longitudinally along a portion of the length of the tube 3004 (i.e., into and out of the paper in FIG. 30). In the illustrated embodiment, the four electrodes 3002A-3002D are spaced equally apart along the circumference of the tube 3004. Electrode 3002A corresponds to channel 1+ and channel 3+. Electrode 3002B corresponds to channel 2+ and channel 4−. Electrode 3002C corresponds to channel 1− and channel 4+. Electrode 3002D corresponds to channel 2− and channel 3−.

As shown in FIG. 30, a four-electrode tube can be used to create four channels by using the diagonal pairs of electrodes for channels 3 and 4. This electrode configuration helps ensure that the tube will always have two good monitoring channels regardless of rotation, and thereby helps reduce or eliminate rotational sensitivity of the tube. A four-electrode tube can also be used to create six channels (e.g., by using the top two electrodes for channel 5 and the bottom two electrodes for channel 6). In one embodiment, the NIM 120 (FIG. 1) is configured to display all four or six channels. In another embodiment, the NIM 120 is configured to determine which of the four or six channels are providing the best signal, and display only the best channel or channels. In one embodiment, tube 3004 includes an identification component (e.g., resistor, RF, magnet, digital) that causes the NIM 120 to switch into a multi-channel mode. The tube may also include one or more LEDs to verify the depth of insertion of the tube. Rotational sensitivity may also be reduced or eliminated by multiplexing a large number of electrode pairs.

Figure 31:
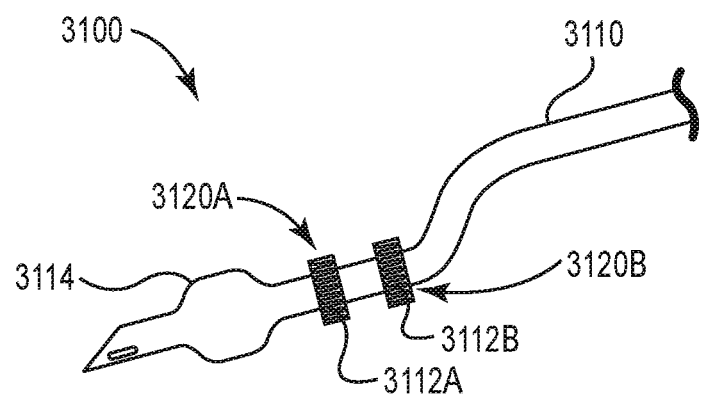
FIG. 31 shows an EMG endotracheal tube with electrodes configured to reduce or eliminate rotational sensitivity according to another embodiment.

FIG. 31 shows an EMG endotracheal tube 3100 with electrodes configured to reduce or eliminate rotational sensitivity according to another embodiment. EMG endotracheal tube 3100 includes tube 3110, primary cuff 3114, and electrode carriers 3120A and 3120B. Each of the electrode carriers 3120A and 3120B is donut-shaped, and surrounds the circumference of the tube 3110. The electrode carriers 3120A and 3120B are spaced apart from each other along the length of the tube 3110. Electrode 3112A is formed on electrode carrier 3120A, and electrode 3112B is formed on electrode carrier 3120B. Each of the electrodes 3112A and 3112B has a sinusoidal wave shape that extends around the circumference of the respective carrier 3120A and 3120B, with peaks and valleys that extend in a longitudinal direction of the tube 3110. In one embodiment, electrode 3112A is a negative electrode and electrode 3112B is a positive electrode. The electrode configuration shown in FIG. 31 helps to reduce or eliminate rotational sensitivity of EMG endotracheal tube 3100.

In another embodiment, EMG endotracheal tube 3100 includes only a single donut-shaped electrode carrier 3120A, and the carrier 3120A is slidably coupled to the tube 3110 to allow the carrier 3120A to longitudinally slide up and down along the length of the tube 3110. In one form of this embodiment, a control member may be attached to the carrier 3120A to selectively cause the carrier 3120A to expand and allow sliding, or to contract and prevent sliding. For example, the control member may cause the carrier 3120A to expand when the carrier 3120A is positioned at the vocal folds such that the carrier 3120A stays at that location while the tube 3110 is allowed to slide through the carrier 3120A. In one embodiment, one or both of the carriers 3120A and 3120B may have a circular cross-sectional shape, or a non-circular cross-sectional shape (e.g., triangular shape).

Figure 32:
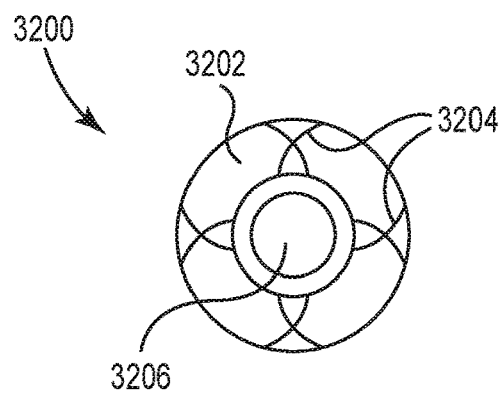
FIG. 32 shows a cuff for an EMG endotracheal tube according to one embodiment.

FIG. 32 shows a cuff 3200 for an EMG endotracheal tube according to one embodiment. Cuff 3200 includes an expandable cuff portion 3202 and tension members 3204. Cuff 3200 also includes a cylindrically-shaped opening 3206 that extends through the cuff 3200, and allows the cuff 3200 to be slid onto an endotracheal tube. Tension members 3204 allow expansion of the cuff portion 3202, but resist torsion and help to minimize rotation of cuff 3200 and the endotracheal tube. In one embodiment, tension members 3204 are self-expanding and are formed from a shape memory material, such as nitinol. In one embodiment, tension members 3204 are a nitinol framework or basket, and the cuff 3200 includes electrodes formed thereon. In one form of this embodiment, the cuff 3200 is configured to atraumatically conform to the shape of the vocal folds.

Figure 33:
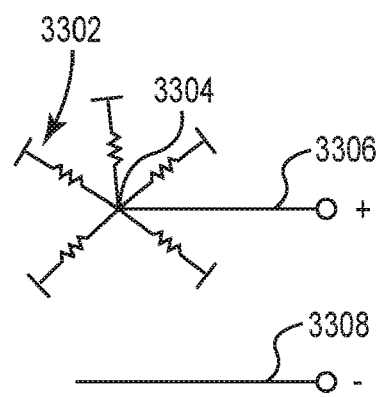
FIG. 33 shows an electrical schematic diagram of an electrode array configured to be used in an EMG endotracheal tube according to one embodiment.

FIG. 33 shows an electrical schematic diagram of an electrode array configured to be used in an EMG endotracheal tube according to one embodiment. The electrode array includes five electrodes 3302 in a star configuration, with the electrodes 3302 sharing a common node 3304. Positive terminal 3306 is connected to the common node 3304. The array also includes terminal 3308. In one embodiment, terminal 3306 and electrodes 3302 are located on the tube, and terminal 3308 is located on a primary or secondary cuff of the tube. The electrode configuration shown in FIG. 33 helps to reduce or eliminate rotational sensitivity of the EMG endotracheal tube. Rotational sensitivity may also be reduced or eliminated by using two ring electrodes that surround the circumference of the tube at two locations (e.g., one ring electrode at the vocal folds and a second ring electrode on a primary or secondary cuff of the tube).

Figure 34:
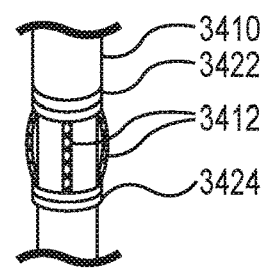
FIG. 34 shows flexible, expanding electrodes configured to be used in an EMG endotracheal tube according to one embodiment.

FIG. 34 shows flexible, expanding electrodes configured to be used in an EMG endotracheal tube according to one embodiment. As shown in FIG. 34, a pair of spaced-apart retaining rings 3422 and 3424 each surround the circumference of tube 3410. The rings 3422 and 3424 hold flexible electrodes 3412 in place between the rings. The electrodes 3412 extend longitudinally along a portion of the length of tube 3410. The closer that rings 3422 and 3424 are positioned toward each other along tube 3410, the farther that the electrodes 3412 extend away from tube 3410. The farther that rings 3422 are positioned away from each other along tube 3410, the closer that the electrodes 3412 are to the tube 3410. The electrodes 3412 may be used to mechanically stimulate the vocal chords. The vocal folds will push the flexible electrodes 3412 inward toward tube 3410.

In the event of movement of an EMG endotracheal tube during surgery, the EMG electrodes on the tube may lose contact with the target muscle and may fail to provide the optimal EMG response. One embodiment provides an EMG endotracheal tube that is insensitive or substantially insensitive to tube movement (rotational and vertical), and provides uninterrupted EMG recording even if the tube moves rotationally or vertically inside the patient during surgery. One form of this embodiment is a tube with three electrodes, with two electrodes configured to be positioned above the vocal folds and one electrode configured to be positioned below the vocal folds. Another form of this embodiment is a tube with four electrodes, with two electrodes configured to be positioned above the vocal folds and two electrodes configured to be positioned below the vocal folds, with the electrodes arranged equally angularly. The electrode configuration for these embodiments differs above and below the level of the vocal folds, which maximizes the signal difference between the activated muscle group and the inactive region. The electrodes above and below the level of the vocal folds improve monitoring of electromyographic (EMG) signals from the muscles of the larynx innervated by the recurrent laryngeal nerves (or the non-recurrent laryngeal nerves) and external branch of the superior laryngeal nerves. The electrodes above and below the level of the vocal folds provide posterior, lateral, and anterior monitoring of the larynx, for example; monitoring left and the right Vocalis muscle, Arytenoids, Thyroarytenoids, Posterior Cricoarytenoids, Lateral Cricoarytenoid, and Cricothyroid muscles. Embodiments that are substantially insensitive to tube position are described in further detail below with reference to FIGS. 35-37.

FIG. 35A shows a first side view (posterior side) of an EMG endotracheal tube 3500 with three electrodes according to one embodiment. FIG. 35B shows a second side view (rotated 90 degrees from the view shown in FIG. 35A) of the EMG endotracheal tube 3500 shown in FIG. 35A according to one embodiment. FIG. 35C is a diagram illustrating a cross-sectional view of the endotracheal tube 3500 shown in FIGS. 35A and 35B according to one embodiment. As shown in FIGS. 35A-35C, endotracheal tube 3500 includes tube 3510, electrodes 3512, and primary cuff 3514. Tube 3510 transports gases to and from the lungs. A proximal end (left end in FIG. 35A) of tube 3510 is configured to be connected to a respirating machine (not shown) for injecting air into the lungs and withdrawing air from the lungs. A cuff inflating conduit (not shown) is configured to be connected to a source of compressed air (not shown) for inflating cuff 3514. After endotracheal tube 3500 is inserted into the trachea of a patient, electrodes 3512 sense EMG signals, which are output to an EMG processing machine (e.g., NIM device 120).

Electrodes 3512 include three electrodes 3512A-3512C, which are formed around a circumference of the tube 3510 and extend in a longitudinal direction of the tube 3510. Electrode 3512B is positioned entirely on the posterior side of the tube 3510 and is also referred to herein as posterior electrode 3512B. Electrodes 3512A and 3512C are positioned primarily on the anterior side of the tube 3510 and are also referred to as anterior electrodes 3512A and 3512C. The anterior side of the tube 3510 is the bottom half of the tube 3510 shown in FIG. 35C, and the posterior side of the tube 3510 is the top half of the tube 3510 shown in FIG. 35C. Each of the electrodes 3512A-3512C is coupled to a respective trace 3524A-3524C (trace 3524A is not visible in the Figures). Traces 3524A-3524C are positioned in a protected (masked) region 3528 of tube 3510. Posterior electrode 3512B is positioned in an exposed (unmasked) region 3526A of tube 3510. Anterior electrodes 3512A and 3512C are positioned in an exposed (unmasked) region 3526B of tube 3510.

In one embodiment, each of the electrodes 3512A-3512C has a length of about one inch, and extends laterally around a circumference of the tube for a distance corresponding to an angle 3522 of about 90 degrees (i.e., each of the electrodes 3512A-3512C has a width of about 25 percent of the total circumference of the tube). The electrodes 3512A-

3512C are laterally spaced apart around the circumference of the tube by a distance corresponding to an angle 3520 of about 30 degrees (i.e., the lateral spacing between each of the electrodes 3512A-3512C is about 8.333 percent of the total circumference of the tube). In another embodiment, each of the electrodes 3512A-3512C extends laterally around a circumference of the tube for a distance corresponding to an angle 3522 of about 60 degrees, and the electrodes 3512A-3512C are laterally spaced apart around the circumference of the tube by a distance corresponding to an angle 3520 of about 60 degrees. In yet another embodiment, the electrodes 3512A-3512C are laterally spaced apart around the circumference of the tube by a distance corresponding to an angle 3520 of greater than about 15 degrees. In one embodiment, the distance around the circumference of the tube from the center of one of the electrodes 3512A-3512C to the center of an adjacent electrode is about 110 degrees to 220 degrees. The posterior electrode 3512B is laterally positioned between the two anterior electrodes 3512A and 3512C, and is longitudinally offset or displaced from the anterior electrodes 3512A and 3512B. The posterior electrode 3512B is positioned closer to the distal end (right side in FIGS. 35A and 35B) of the tube 3510 than the anterior electrodes 3512A and 3512C, and the anterior electrodes 3512A and 3512C are positioned closer to the proximal end (left side in FIGS. 35A and 35B) of the tube 3510 than the posterior electrode 3512B.

Tube 3510 includes an overlap region 3530 where a proximal portion of the posterior electrode 3512B longitudinally overlaps with a distal portion of the anterior electrodes 3512A and 3512C. The electrodes 3512 do not physically overlap each other since they are laterally offset from each other. In one embodiment, the overlap region 3530 is about 0.1 inches long, and the overall length from a proximal end of the anterior electrodes 3512A and 3512C to a distal end of the posterior electrode 3512B is about 1.9 inches. In another embodiment, the overlap region 3530 is about 0.2 inches long, and the overall length from a proximal end of the anterior electrodes 3512A and 3512C to a distal end of the posterior electrode 3512B is about 1.8 inches. Tube 3510 is configured to be positioned such that the vocal folds of a patient are positioned in the overlap region 3530. Thus, the configuration of the electrodes 3512 above the vocal folds is different than the configuration below the vocal folds. The single posterior electrode 3512B is configured to be positioned primarily below the vocal folds, and the two anterior electrodes 3512A and 3512C are configured to be positioned primarily above the vocal folds. It has been determined that the largest response is provided on the anterior side at about 0.5 inches above the vocal folds. In one embodiment, electrodes 3512A and 3512B are used for a first EMG channel, and electrodes 3512C and 3512B are used for a second EMG channel.

FIG. 36A shows a first side view (posterior side) of an EMG endotracheal tube 3600 with four electrodes according to one embodiment. FIG. 36B shows a second side view (rotated 90 degrees from the view shown in FIG. 36A) of the EMG endotracheal tube 3600 shown in FIG. 36A according to one embodiment. FIG. 36C is a diagram illustrating a cross-sectional view of the endotracheal tube 3600 shown in FIGS. 36A and 36B according to one embodiment. As shown in FIGS. 36A-36C, endotracheal tube 3600 includes tube 3610, electrodes 3612, and primary cuff 3614. Tube 3610 transports gases to and from the lungs. A proximal end (left end in FIG. 36A) of tube 3610 is configured to be connected to a respirating machine (not shown) for injecting air into the lungs and withdrawing air from the lungs. A cuff inflating conduit (not shown) is configured to be connected to a source of compressed air (not shown) for inflating cuff 3614. After endotracheal tube 3600 is inserted into the trachea of a patient, electrodes 3612 sense EMG signals, which are output to an EMG processing machine (e.g., NIM device 120).

Electrodes 3612 include four electrodes 3612A-3612D, which are formed around a circumference of the tube 3610 and extend in a longitudinal direction of the tube 3610. Electrodes 3612A and 3612B are positioned entirely on the posterior side of the tube 3610 and are also referred to herein as posterior electrodes 3612A and 3612B. Electrodes 3612C and 3612D are positioned entirely on the anterior side of the tube 3610 and are also referred to as anterior electrodes 3612C and 3612D. The anterior side of the tube 3610 is the bottom half of the tube 3610 shown in FIG. 36C, and the posterior side of the tube 3610 is the top half of the tube 3610 shown in FIG. 36C. Each of the electrodes 3612A-3612D is coupled to a respective trace 3624A-3624D (trace 3624D is not visible in the Figures). Traces 3624A-3624D are positioned in a protected (masked) region 3628 of tube 3610. Posterior electrodes 3612A and 3612B are positioned in an exposed (unmasked) region 3626A of tube 3610. Anterior electrodes 3612C and 3612D are positioned in an exposed (unmasked) region 3626B of tube 3610.

In one embodiment, each of the electrodes 3612A-3612D has a length of about one inch, and extends laterally around a circumference of the tube for a distance corresponding to an angle 3622 of about 60 degrees (i.e., each of the electrodes 3612A-3612D has a width of about 16.666 percent of the total circumference of the tube). The electrodes are laterally spaced apart around the circumference of the tube by a distance corresponding to an angle 3620 of about 30 degrees (i.e., the lateral spacing between each of the electrodes 3612A-3612D is about 8.333 percent of the total circumference of the tube). The posterior electrodes 3612A and 3612B are longitudinally offset or displaced from the anterior electrodes 3612C and 3612D. The posterior electrodes 3612A and 3612B are positioned closer to the distal end (right side in FIGS. 36A and 36B) of the tube 3610 than the anterior electrodes 3612C and 3612D, and the anterior electrodes 3612C and 3612D are positioned closer to the proximal end (left side in FIGS. 36A and 36B) of the tube 3610 than the posterior electrodes 3612A and 3612B.

Tube 3610 includes an overlap region 3630 where a proximal portion of the posterior electrodes 3612A and 3612B longitudinally overlap with a distal portion of the anterior electrodes 3612C and 3612D. The electrodes 3612 do not physically overlap each other since they are laterally offset from each other. In one embodiment, the overlap region 3630 is about 0.1 inches long, and the overall length from a proximal end of the anterior electrodes 3612C and 3612D to a distal end of the posterior electrodes 3612A and 3612B is about 1.9 inches. In another embodiment, the overlap region 3630 is about 0.2 inches long, and the overall length from a proximal end of the anterior electrodes 3612C and 3612D to a distal end of the posterior electrodes 3612A and 3612B is about 1.8 inches. Tube 3610 is configured to be positioned such that the vocal folds of a patient are positioned in the overlap region 3630. Thus, the configuration of the electrodes 3612 above the vocal folds is different than the configuration below the vocal folds. The posterior electrodes 3612A and 3612B are configured to be positioned primarily below the vocal folds, and the anterior electrodes 3612C and 3612D are configured to be positioned primarily above the vocal folds. In one embodiment, electrodes 3612A and 3612C are used for a first EMG channel, and electrodes 3612B and 3612D are used for a second EMG channel. In another embodiment, electrodes 3612A and 3612D are used for a first EMG channel, and electrodes 3612B and 3612C are used for a second EMG channel.

FIG. 37A shows a first side view (posterior side) of an EMG endotracheal tube 3700 with four electrodes according to another embodiment. FIG. 37B shows a second side view (rotated 90 degrees from the view shown in FIG. 37A) of the EMG endotracheal tube 3700 shown in FIG. 37A according to one embodiment. As shown in FIGS. 37A and 36B, endotracheal tube 3700 includes tube 3710, electrodes 3712, and primary cuff 3714. Tube 3710 transports gases to and from the lungs. A proximal end (left end in FIG. 37A) of tube 3710 is configured to be connected to a respirating machine (not shown) for injecting air into the lungs and withdrawing air from the lungs. A cuff inflating conduit (not shown) is configured to be connected to a source of compressed air (not shown) for inflating cuff 3714. After endotracheal tube 3700 is inserted into the trachea of a patient, electrodes 3712 sense EMG signals, which are output to an EMG processing machine (e.g., NIM device 120).

Electrodes 3712 include four electrodes 3712A-3712D, which are formed around a circumference of the tube 3710 and extend in a longitudinal direction of the tube 3710. Each of the electrodes 3712A-3712D is coupled to a respective trace 3724A-3724D (traces 3724A and 3724D are not visible in the Figures). Traces 3724A-3724D are positioned in a protected (masked) region 3728 of tube 3710. Electrodes 3712C and 3712D are positioned in an exposed (unmasked) region 3726A of tube 3710. Electrodes 3712A and 3712B are positioned in an exposed (unmasked) region 3726B of tube 3710.

In one embodiment, each of the electrodes 3712A-3712D has a length of about one inch. In one embodiment, each of the electrodes 3712A and 3712B extends laterally around a circumference of the tube for a distance corresponding to an angle of about 140 degrees (i.e., each of the electrodes 3712A and 3712B has a width of about 38.888 percent of the total circumference of the tube). In one embodiment, each of the electrodes 3712C and 3712D extends laterally around a circumference of the tube for a distance corresponding to an angle of about 110 degrees (i.e., each of the electrodes 3712C and 3712D has a width of about 30.555 percent of the total circumference of the tube). Electrodes 3712A and 3712B are laterally spaced apart from each other around the circumference of the tube by a distance corresponding to an angle of about 40 degrees (i.e., the lateral spacing between the electrodes 3712A and 3712B is about 11.111 percent of the total circumference of the tube). Electrodes 3712C and 3712D are laterally spaced apart from each other around the circumference of the tube by a distance corresponding to an angle of about 70 degrees (i.e., the lateral spacing between the electrodes 3712C and 3712D is about 19.444 percent of the total circumference of the tube). The electrodes 3712A and 3712B are longitudinally offset or displaced from the electrodes 3712C and 3712D. The electrodes 3712C and 3712D are positioned closer to the distal end (right side in FIGS. 37A and 37B) of the tube 3710 than the electrodes 3712A and 3712B, and the electrodes 3712A and 3712B are positioned closer to the proximal end (left side in FIGS. 37A and 37B) of the tube 3710 than the electrodes 3712C and 3712D.

Tube 3710 includes a separation region 3730 where a proximal end of the electrodes 3712C and 3712D is longitudinally separated from a distal end of the electrodes 3712A and 3712B. In one embodiment, the separation region 3730 is about 0.1 inches long, and the overall length from a proximal end of the electrodes 3712A and 3712B to a distal end of the electrodes 3712C and 3712D is about 2.1 inches. In another embodiment, the separation region 3730 is about 0.2 inches long, and the overall length from a proximal end of the electrodes 3712A and 3712B to a distal end of the electrodes 3712C and 3712D is about 2.2 inches. Tube 3710 is configured to be positioned such that the vocal folds of a patient are positioned in the separation region 3730. Thus, the configuration of the electrodes 3712 above the vocal folds is different than the configuration below the vocal folds. The electrodes 3712C and 3712D are configured to be positioned primarily below the vocal folds, and the electrodes 3712A and 3712B are configured to be positioned primarily above the vocal folds.

Figure 38:
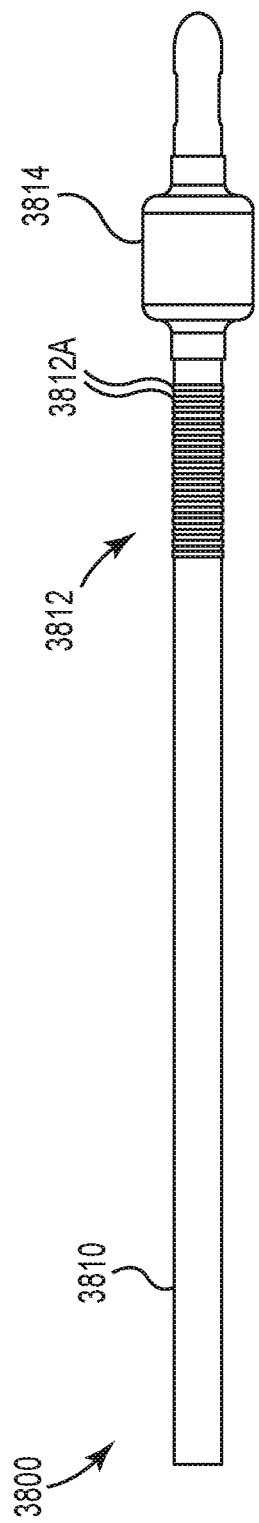
FIG. 38 shows a side view of an EMG endotracheal tube with a plurality of ring electrodes according to one embodiment.

FIG. 38 shows a side view of an EMG endotracheal tube 3800 with a plurality of ring electrodes according to one embodiment. As shown in FIG. 38, endotracheal tube 3800 includes tube 3810, electrodes 3812, and primary cuff 3814. Tube 3810 transports gases to and from the lungs. A proximal end (left end in FIG. 38) of tube 3810 is configured to be connected to a respirating machine (not shown) for injecting air into the lungs and withdrawing air from the lungs. A cuff inflating conduit (not shown) is configured to be connected to a source of compressed air (not shown) for inflating cuff 3814. After endotracheal tube 3800 is inserted into the trachea of a patient, electrodes 3812 sense EMG signals, which are output to an EMG processing machine (e.g., NIM device 120).

Electrodes 3812 include a plurality of ring electrodes 3812A. In one embodiment, each of the ring electrodes 3812A completely surrounds a circumference of the tube 3810. In one embodiment, electrodes 3812 include sixteen ring electrodes 3812A that are longitudinally separated from each other along the length of the tube by a distance of about 0.05 inches, and have an overall length in the longitudinal direction of the tube of about 1.55 inches.

FIGS. 39A-39E show EMG endotracheal tubes with tube placement markings according to various embodiments. In one embodiment, the tube markings shown in FIGS. 39A-39E are formed from a radio opaque material.

As shown in FIG. 39A, EMG endotracheal tube 3900A includes three bands 3902, 3904, and 3906, and a vertical line segment 3908. The bands 3902, 3904, and 3906, and the vertical line segment 3908, are positioned on an electrode region of the tube 3900A, and facilitate proper longitudinal and rotational positioning of the electrodes of tube 3900A with respect to a patient's anatomy. Bands 3902, 3904, and 3906 are positioned adjacent to each other, with band 3904 positioned between band 3902 and 3906. In one embodiment, each of the bands 3902, 3904, and 3906 surrounds a circumference of the tube 3900A or a portion of the circumference of the tube 3900A, and the bands 3902, 3904, and 3906 have an overall length along a longitudinal axis of the tube 3900A that is the same or substantially the same as the length of the electrodes of tube 3900A. In one embodiment, bands 3902 and 3906 have substantially the same length, which is about twice as long as the length of band 3904. Bands 3902, 3904, and 3906 are solid color bands in one embodiment, and at least two different colors are used for the three bands. In one embodiment, bands 3902, 3904, and 3906 are each a solid color band with a different color than the other bands (i.e., 3 different solid colors are used for the three bands). In one form of this embodiment, band 3902 is a green band, band 3904 is a white band, and band 3906 is a blue band. The colors are selected in one embodiment to differentiate the bands from blood and surrounding tissue. Vertical line segment 3908 extends in a longitudinal direction along tube 3900A, and has a length that is the same or substantially the same as the overall length of the bands 3902, 3904, and 3906.

As shown in FIG. 39B, EMG endotracheal tube 3900B includes band 3910, vertical line segment 3914, and horizontal line segments 3916, 3918, and 3920. The band 3910 and the line segments 3914, 3916, 3918, and 3920 are positioned on an electrode region of the tube 3900B, and facilitate proper longitudinal and rotational positioning of the electrodes of tube 3900B with respect to a patient's anatomy. In one embodiment, band 3910 surrounds a circumference of the tube 3900B, and has a length along a longitudinal axis of the tube 3900B that is the same or substantially the same as the length of the electrodes of tube 3900B. Band 3910 is a solid color band in one embodiment. In one embodiment, band 3910 is a white band. In another embodiment, band 3910 is a blue band. The color is selected in one embodiment to differentiate the band from blood and surrounding tissue.

Vertical line segment 3914 extends in a longitudinal direction along tube 3900B, and has a length that is the same or substantially the same as the length of the band 3910. Each of the horizontal line segments 3916, 3918, and 3920 intersects the vertical line segment 3914 and extends in a lateral direction around a portion of the circumference of the tube 3900B. The horizontal line segments 3916, 3918, and 3920 are each centered on the vertical line segment 3914, and are spaced apart from each other along a longitudinal axis of the tube 3900B. Horizontal line segment 3918 is positioned between segments 3916 and 3920. Horizontal line segments 3916 and 3920 have the same length in one embodiment, which is less than the length of segment 3918. In one embodiment, segment 3918 has a length that is at least about twice as long as the length of each of the segments 3916 and 3920.

As shown in FIG. 39C, EMG endotracheal tube 3900C includes band 3922, vertical line segment 3926, horizontal line segment 3928, and diagonal line segments 3930 and 3932. The band 3922 and the line segments 3926, 3928, 3930, and 3932 are positioned on an electrode region of the tube 3900C, and facilitate proper longitudinal and rotational positioning of the electrodes of tube 3900C with respect to a patient's anatomy. In one embodiment, band 3922 surrounds a circumference of the tube 3900C, and has a length along a longitudinal axis of the tube 3900C that is the same or substantially the same as the length of the electrodes of tube 3900C. Band 3922 is a solid color band in one embodiment. In one embodiment, band 3922 is a white band. In another embodiment, band 3922 is a blue band. The color is selected in one embodiment to differentiate the band from blood and surrounding tissue.

The line segments 3926, 3928, 3930, and 3932 all intersect at a common point 3924. Vertical line segment 3926 extends in a longitudinal direction along tube 3900C, and has a length that is the same or substantially the same as the length of the band 3922. The horizontal line segment 3928 is centered on the vertical line segment 3926 and extends in a lateral direction around a portion of the circumference of the tube 3900C. Diagonal line segments 3930 and 3932 extend longitudinally and laterally along tube 3900C and intersect each other at common point 3924 to form an x-type marking.

As shown in FIG. 39D, EMG endotracheal tube 3900D includes band 3934, triangular markings 3936 and 3940, and vertical line segment 3942, which are positioned on an electrode region of the tube 3900D, and facilitate proper longitudinal and rotational positioning of the electrodes of tube 3900D with respect to a patient's anatomy. In one embodiment, band 3934 surrounds a circumference of the tube 3900D, and has a length along a longitudinal axis of the tube 3900D that is the same or substantially the same as the length of the electrodes of tube 3900D. Band 3934 is a solid color band in one embodiment. In one embodiment, band 3934 is a white band.

Each of the triangular markings 3936 and 3940 according to one embodiment has substantially the shape of an isosceles triangle. Each of the triangular markings 3936 and 3940 has a base segment that extends laterally around a portion of the circumference of the tube 3900D, and two equal sides that extend away from the base portion and meet at an apex of the triangle. The apexes of the triangular markings 3936 and 3940 share a common point 3938. Each of the triangular markings 3936 and 3940 is a solid color marking in one embodiment. In one embodiment, the color of marking 3936 is different than the color of marking 3940. In one form of this embodiment, marking 3936 is a green marking, and marking 3940 is a blue marking. The colors are selected in one embodiment to differentiate the markings from blood and surrounding tissue.

Vertical line segment 3942 extends in a longitudinal direction along tube 3900D from the middle of the base segment of the triangular marking 3936 to the middle of the base segment of the triangular marking 3936, and intersects the common point 3938. Vertical line segment 3942 has a length that is the same or substantially the same as the length of the band 3934.

Figure 39E:
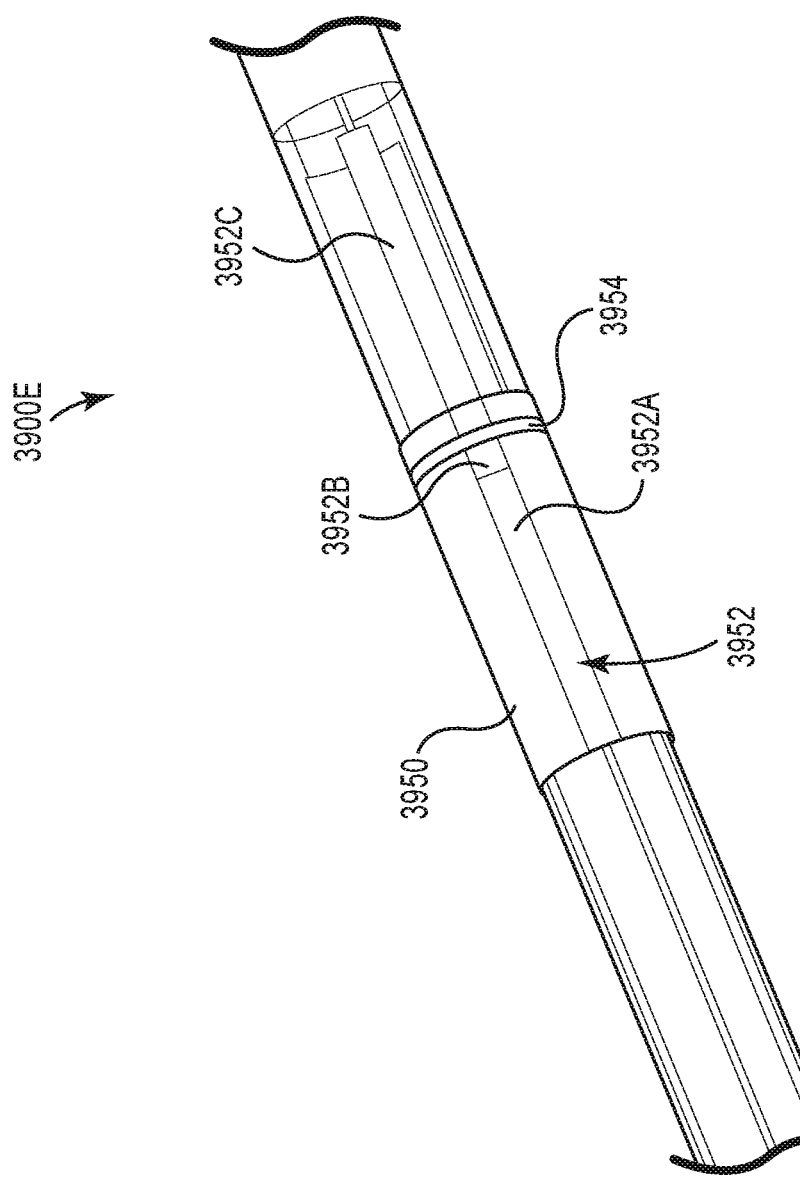

As shown in FIG. 39E, EMG endotracheal tube 3900E includes band 3950, vertical line or strip 3952, and horizontal line or strip 3954, which are positioned on an electrode region of the tube 3900E, and facilitate proper longitudinal and rotational positioning of the electrodes of tube 3900E with respect to a patient's anatomy. In one embodiment, band 3950 surrounds a circumference of the tube 3900E. Band 3950 is a solid color band in one embodiment.

Vertical strip 3952 extends in a longitudinal direction along tube 3900E, and has a length that is the same or substantially the same as the length of the electrodes of tube 3900E. Vertical strip 3952 includes two end portions 3952A and 3952C separated by a middle portion 3952B. In one embodiment, the end portions 3952A and 3952C have a substantially equal length, which is about four times longer than the length of the middle portion 3952B. Band 3950 extends from a bottom end of vertical strip end portion 3952A to a top end of vertical strip middle portion 3952B.

Horizontal strip 3954 intersects the vertical strip 3952 at the middle portion 3952B, and extends in a lateral direction around at least a portion of the circumference of the tube 3900E. In one embodiment, band 3950 is a solid color band (e.g., gray), and horizontal strip 3954 is a solid color strip (e.g., white). In one embodiment, vertical strip portions 3952A and 3952C are formed from the same solid color (e.g., blue), which is different than the solid color of vertical strip portion 3952B (e.g., white). The colors are selected in one embodiment to differentiate the bands from blood and surrounding tissue.

One embodiment is directed to an apparatus for monitoring EMG signals of a patient's laryngeal muscles. The apparatus includes an endotracheal tube having an exterior surface and conductive ink electrodes formed on the exterior surface. The conductive ink electrodes are configured to receive the EMG signals from the laryngeal muscles when the endotracheal tube is placed in a trachea of the patient. At least one conductor is coupled to the conductive ink electrodes and is configured to carry the EMG signals received by the conductive ink electrodes to a processing apparatus.

The conductive ink electrodes according to one embodiment comprise a silver filled polymer conductive ink or a carbon conductive ink. In one embodiment, the conductive ink electrodes include at least six conductive ink electrodes that extend longitudinally along a length of the tube and that are spaced apart to surround a circumference of the endotracheal tube. The apparatus according to one embodiment includes an inflatable cuff connected to the endotracheal tube, and at least one conductive ink electrode formed on the inflatable cuff and configured to sense EMG signals from vocal folds of the patient. In one embodiment, at least one of a light source and a magnet is positioned on the endotracheal tube near the conductive ink electrodes.

One embodiment of the apparatus includes a coupling adapter configured to allow a proximal end of the endotracheal tube to rotate with respect to a distal end of the endotracheal tube. In one embodiment, the apparatus includes a first rib surrounding the endotracheal tube and positioned above the conductive ink electrodes on the endotracheal tube, and a second rib surround the endotracheal tube and positioned below the conductive ink electrodes on the endotracheal tube. At least one automatic periodic stimulation (APS) electrode is formed on the endotracheal tube in one embodiment, and the processing apparatus is configured to determine a position of the endotracheal tube based on signals generated by the at least one APS electrode. In one embodiment, at least one of a conducting hydro gel and an expandable, conductive foam is formed on the electrodes.

The endotracheal tube comprises a braided endotracheal tube in one embodiment. In one embodiment, the electrodes include four electrodes and the at least one conductor includes at least four pairs of conductors, and each pair of conductors is coupled to a different pair of the four electrodes to provide at least four channels of EMG signals from the four electrodes. In one form of this embodiment, the processing apparatus is configured to analyze the four channels of EMG signals and identify a subset of the four channels to display based on the analysis. At least one wireless sensor is provided on the endotracheal tube in one embodiment, with the at least one wireless sensor configured to wirelessly transmit information to the processing apparatus. In one embodiment, each of the electrodes is at least about 1.9 inches in length. The electrodes form an electrode grid with at least two horizontal electrodes and at least two vertical electrodes. In one embodiment the apparatus includes at least one of a temperature sensing element, fiber optic element, and video element. In one embodiment, the apparatus includes at least one of a strain measurement element, an acceleration measurement element, and a piezoelectric element.

Another embodiment is directed to a method of monitoring EMG signals of a patient's laryngeal muscles. The method includes providing an endotracheal tube having an exterior surface and conductive ink electrodes formed on the exterior surface. The EMG signals from the laryngeal muscles are sensed with the conductive ink electrodes when the endotracheal tube is placed in a trachea of the patient. The EMG signals sensed by the conductive ink electrodes are output to a processing apparatus.

Another embodiment is directed to an apparatus for monitoring EMG signals of a patient's laryngeal muscles. The apparatus includes an endotracheal tube having an exterior surface. Four electrodes are formed on the exterior surface of the endotracheal tube. The four electrodes are configured to receive the EMG signals from the laryngeal muscles when the endotracheal tube is placed in a trachea of the patient. At least four pairs of conductors are coupled to the four electrodes and configured to carry the EMG signals received by the electrodes to a processing apparatus. Each pair of the conductors is coupled to a different pair of the four electrodes to provide at least four channels of EMG signals from the four electrodes.

Although embodiments set forth herein have been described in the context of an EMG endotracheal tube, it will be understood that the techniques are also applicable to other types of devices, such as a tube for monitoring a patient's anal sphincter or urethral sphincter.

Although the present disclosure has been described with reference to preferred embodiments, workers skilled in the art will recognize that changes can be made in form and detail without departing from the spirit and scope of the present disclosure.

What is claimed is:

1. A method, comprising:
providing an endotracheal tube having an exterior surface and at least four conductive ink electrodes on the exterior surface, wherein the at least four conductive ink electrodes include at least two stimulating electrodes and at least two monitoring electrodes;
stimulating tissue of a patient with the stimulating electrodes; and
monitoring at least one nerve of the patient using the monitoring electrodes during the stimulation.

2. The method of claim 1, wherein the at least four conductive ink electrodes are printed directly on the exterior surface of the endotracheal tube.

3. The method of claim 1, and further comprising:
receiving, with the stimulating electrodes, a stimulation signal from a stimulation channel of a multi-channel nerve integrity monitor device.

4. The method of claim 3, and further comprising:
sending, with the monitoring electrodes, a monitoring signal to a monitoring channel of the multi-channel nerve integrity monitor device.

5. The method of claim 4, and further comprising:
carrying the stimulation signal and the monitoring signal between the electrodes and the multi-channel nerve integrity monitor device with a plurality of conductors.

6. The method of claim 1, and further comprising:
analyzing, with a multi-channel nerve integrity monitor device, multiple channels of monitoring signals received from the monitoring electrodes; and
identifying, with the multi-channel nerve integrity monitor device, a subset of the multiple channels to display based on the analysis.

7. The method of claim 1, wherein at least two of the at least four conductive ink electrodes are laterally and longitudinally offset from other ones of the at least four conductive ink electrodes.

8. The method of claim 1, and further comprising:
positioning at least a portion of the endotracheal tube in a region of a trachea of the patient with at least some of the conductive ink electrodes in contact with at least a portion of the trachea; and
stimulating vocal folds of the patient with the stimulating electrodes.

9. The method of claim 1, wherein the stimulating electrodes include at least one automatic periodic stimulation (APS) electrode.

10. The method of claim 1, and further comprising:
monitoring the at least one nerve of the patient using at least one of the stimulating electrodes.

11. A system, comprising:

an endotracheal tube having an exterior surface and at least four conductive ink electrodes on the exterior surface, wherein the at least four conductive ink electrodes include at least two stimulating electrodes configured to stimulate tissue of a patient, and wherein the at least four conductive ink electrodes include at least two monitoring electrodes configured to monitor at least one nerve of the patient; and a multi-channel nerve integrity monitor device configured to send a stimulation signal to the stimulating electrodes via a first channel, and configured to receive a monitoring signal from the monitoring electrodes via a second channel.

12. The system of claim 11, wherein the multi-channel nerve integrity monitor device includes at least four channels for sending stimulation signals to the stimulating electrodes and receiving monitoring signals from the monitoring electrodes.

13. The system of claim 11, wherein the multi-channel nerve integrity monitor device is configured to analyze multiple channels of monitoring signals received from the monitoring electrodes, and identify a subset of the multiple channels to display based on the analysis.

14. The system of claim 11, wherein the at least four conductive ink electrodes are printed directly on the exterior surface of the endotracheal tube.

15. The system of claim 11, and further comprising:

a plurality of conductors configured to carrying the stimulation signal and the monitoring signal between the electrodes and the multi-channel nerve integrity monitor device.

16. The system of claim 11, wherein at least two of the at least four conductive ink electrodes are laterally and longitudinally offset from other ones of the at least four conductive ink electrodes.

17. The system of claim 11, wherein the stimulating electrodes are configured to stimulate tissue in a region of vocal folds of the patient.

18. The system of claim 17, wherein the stimulating electrodes include a first one of the stimulating electrodes that is laterally and longitudinally offset from a second one of the stimulating electrodes.

19. The system of claim 11, wherein the stimulating electrodes include at least one automatic periodic stimulation (APS) electrode.

20. The system of claim 11, wherein at least one of the stimulating electrodes is also configured to monitor the at least one nerve of the patient.

* * * * *